US00RE39221E

(19) United States
(12) Reissued Patent
Raffa et al.

(10) Patent Number: US RE39,221 E
(45) Date of Reissued Patent: Aug. 1, 2006

(54) COMPOSITION COMPRISING A TRAMADOL MATERIAL AND ACETAMINOPHEN AND ITS USE

(75) Inventors: Robert B. Raffa, Norristown, PA (US); Jeffrey L. Vaught, Glenmoore, PA (US)

(73) Assignee: Ortho-McNeil Pharmaceutical, Inc., Raritan, NJ (US)

(21) Appl. No.: 10/761,096

(22) Filed: Jan. 20, 2004

Related U.S. Patent Documents

Reissue of:
(64) Patent No.: 5,336,691
Issued: Aug. 9, 1994
Appl. No.: 07/974,865
Filed: Nov. 10, 1992

U.S. Applications:
(63) Continuation-in-part of application No. 07/755,924, filed on Sep. 6, 1991, now abandoned.

(51) Int. Cl.
*A61K 31/16* (2006.01)

(52) U.S. Cl. ..... 514/629; 514/646; 514/649; 514/650

(58) Field of Classification Search ..... 514/629, 514/646, 649, 650
See application file for complete search history.

(56) References Cited

U.S. PATENT DOCUMENTS

| | | | | |
|---|---|---|---|---|
| 2,770,569 | A | 11/1956 | Fromherz et al. | 167/65 |
| 3,652,589 | A * | 3/1972 | Flick et al. | 548/578 |
| 3,773,955 | A | 11/1973 | Pachter et al. | 424/260 |
| 3,830,934 | A | 8/1974 | Flick et al. | 424/330 |
| 4,132,788 | A | 1/1979 | Wong | 424/232 |
| 4,237,140 | A | 12/1980 | Dudzinski | 424/260 |
| 4,260,629 | A | 4/1981 | Schmidt et al. | 424/274 |
| 4,322,427 | A | 3/1982 | Buyniski et al. | 424/260 |
| 4,571,400 | A | 2/1986 | Arnold | 514/282 |
| 4,601,894 | A | 7/1986 | Hanna et al. | 424/19 |
| 4,631,284 | A | 12/1986 | Salpekar et al. | 514/277 |
| 4,730,007 | A | 3/1988 | Ehrenpreis | 514/561 |
| 4,769,372 | A | 9/1988 | Kreek | 514/282 |
| 4,806,543 | A | 2/1989 | Choi | 514/464 |
| 4,829,064 | A | 5/1989 | Sunshine et al. | 514/255 |
| 4,943,565 | A | 7/1990 | Tencza et al. | 514/161 |
| 5,223,541 | A | 6/1993 | Maryanoff et al. | 514/644 |
| 5,317,022 | A | 5/1994 | Borsodi et al. | 514/282 |
| 5,352,680 | A | 10/1994 | Portoghese et al. | 514/279 |
| 5,468,744 | A | 11/1995 | Raffa et al. | 514/282 |
| 5,516,803 | A | 5/1996 | Raffa | 514/570 |
| 6,562,865 | B1 | 5/2003 | Codd et al. | 514/456 |

FOREIGN PATENT DOCUMENTS

| | | |
|---|---|---|
| EP | 0 017 102 A1 | 10/1980 |
| EP | 0 358 107 A2 | 3/1990 |
| EP | 0 240 904 B1 | 7/1992 |
| EP | 0 358 105 B1 | 3/1994 |
| EP | 0 227 836 B1 | 12/1997 |
| JP | 54-92631 | 7/1979 |
| JP | 55-129225 | 10/1980 |
| JP | 55-154917 | 12/1980 |
| JP | 57-128626 | 8/1982 |

OTHER PUBLICATIONS

Budavari, Susan, editor, *The Merck Index,* 11th Edition, Merck & Co., Inc., Rahway, N.J., 1989, pp. 8 and 1506.

In the United States District Court for the District of New Jersey, Civil Action No. 02–2707(JCL), *Ortho–McNeil Pharmaceutical, Inc.,* v. *Kali Laboratories, Inc:.* First Amended Complaint for Patent Infringement, Jul. 27, 2005.

In the United States District Court for the District of New Jersey, Civil Action No. 02–2707(JCL), *Ortho–McNeil Pharmaceutical, Inc.,* v. *Kali Laboratories, Inc:.* Defendant Kali Laboratories, Inc.'s Second Amended Answer, Counterclaim, and Jury Demand and Defendants Par Pharmaceutical Companies, Inc.'s and Par Pharmaceutical, Inc.'s Answer, Counterclaim, and Jury Demand, Aug. 25, 2005.

In the United States District Court for the District of New Jersey, Civil Action No. 04–886(HAA), *Ortho–McNeil Pharmaceutical, Inc.,* v. *Teva Pharmaceutical Industries Ltd.,* Videotape Deposition of Eric Smith, Ph.D., May 13, 2005.

In the United States District Court for the District of New Jersey, Civil Action No. 04–886(HAA), *Ortho–McNeil Pharmaceutical, Inc.,* v. *Teva Pharmaceutical Industries Ltd.,* Deposition of Dr. David Schoenfeld, May 17, 2005.

In the United States District Court for the District of New Jersey, Civil Action No. 04–886(HAA), *Ortho–McNeil Pharmaceutical, Inc.,* v. *Teva Pharmaceutical Industries Ltd.,* Deposition of Donald Stanski, M.D., May 27, 2005 (REDACTED).

In the United States District Court for the District of New Jersey, Civil Action No. 04–886(HAA), *Ortho–McNeil Pharmaceutical, Inc.,* v. *Teva Pharmaceutical Industries Ltd.,* Deposition of Dr. Gilbert Fanciullo, Jun. 14, 2005.

In the United States District Court for the Eastern District of Michigan, Civil Action No. 2:04CV73698, *Ortho–McNeil Pharmaceutical, Inc.,* v. *Caraco Pharmaceutical Laboratories, Ltd.,* Caraco's Supplemental Response to Plaintiff's First Set of Interrogatories, Jun. 14, 2005, REDACTED.

(Continued)

*Primary Examiner*—Dwayne Jones
(74) *Attorney, Agent, or Firm*—Woodcock Washburn LLP

(57) ABSTRACT

This invention relates to a composition comprising a tramadol material and acetaminophen, and its use. As used herein tramadol refers to various forms of tramadol. The compositions are pharmacologically useful in treating pain and tussive conditions. The compositions are also subject to less opioid side-effects such as abuse liability, tolerance, constipation and respiratory depression. Furthermore, where the components of the compositions are within certain ratios the pharmacological effects of the compositions are superadditive (synergistic).

63 Claims, 1 Drawing Sheet

OTHER PUBLICATIONS

In the United States District Court for the Eastern District of Michigan, Civil Action No. 2:04CV73698, *Ortho–McNeil Pharmaceutical, Inc.,* v. *Caraco Pharmaceutical Laboratories, Ltd.,* Caraco's Second Supplemental Response to Plaintiff's First Set of Interrogatories, Jun. 24, 2005.

In the United States District Court for the Eastern District of Michigan, Civil Action No. 2:04CV73698, *Ortho–McNeil Pharmaceutical, Inc.,* v. *Caraco Pharmaceutical Laboratories, Ltd.,* Caraco's Motion for Summary Judgment of Non–Infringement, Aug. 5, 2005, REDACTED.

In the United States District Court for the Eastern District of Michigan, Civil Action No. 2:04CV73698, *Ortho–McNeil Pharmaceutical, Inc.,* v. *Caraco Pharmaceutical Laboratories, Ltd.,* Expert Report of Donald R. Stanski, M.D. Aug. 5, 2005, REDACTED.

In the United States District Court for the Eastern District of Michigan, Civil Action No. 2:04CV73698, *Ortho–McNeil Pharmaceutical, Inc.,* v. *Caraco Pharmaceutical Laboratories, Ltd.,* Expert Report of Eric P. Smith, Ph.D., Aug. 8, 2005.

In the United States District Court for the Eastern District of Michigan, Civil Action No. 2:04CV73698, *Ortho–McNeil Pharmaceutical, Inc.,* v. *Caraco Pharmaceutical Laboratories, Ltd.,* Ortho–McNeil's Opposition to Caraco's Motion for Summary Judgment of Non–Infringement, Aug. 29, 2005, REDACTED.

In the United States District Court For The District of New Jersey, Civil Action No. 02–5707 (JCL), *Ortho–McNeil Pharmaceutical, Inc.* v. *Kali Laboratories, Inc.:* Ortho–McNeil's Brief in Opposition to Kali's Motion for Summary Judgment of Invalidity and Noninfringement of U.S. Pat. No. 5,336,691: Claim 6 (Jul. 21, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Ortho–McNeil's Rule 56.1 Statement of Disputed Material Facts in Opposition to Defendant Kali's Laboratories' Motion for Summary Judgment of Invalidity and Noninfringement of U.S. Pat. No. 5,336,691: Claim 6 (Jul. 21, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Reply Brief in Support of Defendant Kali Laboratories' Motion for Summary Judgment of Invalidity and Noninfringement of U.S. Pat. No. 5,336,691: Claim 6 (Aug. 23, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Ortho–McNeil's Surreply in Opposition to Kali's Motion for Summary Judgment of Invalidity and Noninfringement of U.S. Pat. No. 5,336,691: Claim 6 (Sep. 21, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Rule 56.1 Statement of Undisputed Facts for Defendant Kali Laboratories' Motion for Summary Judgment of Invalidity Under the 35 U.S.C. § 102(b) Public Use Bar (May 28, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Ortho–McNeil's Brief in Opposition to Kali's Motion for Summary Judgment of Invalidity Under the 35 U.S.C. § 102(b) Public Use Bar (Jul. 21, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Ortho–McNeil's Statement of Material Facts in Dispute With Respect to Kali's Motion for Summary Judgment of Invalidity Under the 35 U.S.C. § 102(b) Public Use Bar (Jul. 21, 2004).

In the United States District Court For The District of New Jersey, Civil Action No. 02–5707 (JCL), *Ortho–McNeil Pharmaceutical, Inc.* v. *Kali Laboratories, Inc.:* Reply Brief in Support of Defendant Kali Laboratories' Motion for Summary Judgment of Invalidity Under the 35 U.S.C. § 102(b) Public Use Bar (Aug. 23, 2004).

In the United States District Court For The District of New Jersey, Civil Action No. 02–5707 (JCL), *Ortho–McNeil Pharmaceutical, Inc.* v. *Kali Laboratories, Inc.:* vol. 1A of Materials Supporting Ortho–McNeil's Oppositions to Kali's Motions for Summary Judgment: Declaration of Jeffrey P. Kushan (Part 1 of 2),with attachments 1 thru 9, Jul. 21, 2004, vol. 1B of Materials Supporting Ortho–McNeil's Oppositions to Kali's Motions for Summary Judgment: Declaration of Jeffrey P. Kushan (Part 2 of 2) with attachments 10 thru 30, vol. 1C pf Materials Supporting Ortho–McNeil's Oppositions to Kali's Motion for Summary Judgment–with attachments Tabs 1 thru 4 (all dated on or about Jul. 21, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Deposition of Robert B. Raffa (2nd Day) (Apr. 21, 2004).

In the United States District Court For The District of New Jersey, Civil Action No. 02–5707 (JCL), *Ortho–McNeil Pharmaceutical, Inc.* v. *Kali Laboratories, Inc.:* Deposition of Ronald Tallarida, Ph.D, (Mar. 24, 2004).

In the United States District Court For The District of New Jersey, Civil Action No. 02–5707 (JCL), *Ortho–McNeil Pharmaceutical, Inc.* v. *Kali Laboratories, Inc.:* Deposition of Ralph Palo (Mar. 18, 2004).

In the United States District Court For The District of New Jersey, Civil Action No. 02–5707 (JCL), *Ortho–McNeil Pharmaceutical, Inc.* v. *Kali Laboratories, Inc.:* Deposition of Ravi Desiraju (Jan. 21, 2004).

In the United States District Court For The District of New Jersey, Civil Action No. 02–5707 (JCL), *Ortho–McNeil Pharmaceutical, Inc.* v. *Kali Laboratories, Inc.:* Deposition of Natasha Rogozenski (Mar. 30, 2004).

In the United States District Court For The District of New Jersey, Civil Action No. 02–5707 (JCL), *Ortho–McNeil Pharmaceutical, Inc.* v. *Kali Laboratories, Inc.:* Deposition of Robert Medve, M.D. (Dec. 2, 2003).

In the United States District Court For The District of New Jersey, Civil Action No. 02–5707 (JCL), *Ortho–McNeil Pharmaceutical, Inc.* v. *Kali Laboratories, Inc.:* Deposition of Marc Kamin (Dec. 4, 2003).

In the United States District Court For The District of New Jersey, Civil Action No. 02–5707 (JCL), *Ortho–McNeil Pharmaceutical, Inc.* v. *Kali Laboratories, Inc.:* Deposition of Abraham Sunshine (Mar. 12, 2004).

In the United States District Court For The District of New Jersey, Civil Action No. 02–5707 (JCL), *Ortho–McNeil Pharmaceutical, Inc.* v. *Kali Laboratories, Inc.:* Deposition of Stephen Cooper, Ph.D. (Mar. 26, 2004).

In the United States District Court For The District of New Jersey, Civil Action No. 02–5707 (JCL), *Ortho–McNeil Pharmaceutical, Inc.* v. *Kali Laboratories, Inc.:* Deposition of Marvin Ladov (Feb. 11, 2004).

In the United States District Court For The District of New Jersey, Civil Action No. 02–5707 (JCL), *Ortho–McNeil Pharmaceutical, Inc.* v. *Kali Laboratories, Inc.:* Deposition of Nicholas Landekic (Apr. 5, 2004).

In the United States District Court For The District of New Jersey, Civil Action No. 02–5707 (JCL), *Ortho–McNeil Pharmaceutical, Inc.* v. *Kali Laboratories, Inc.:* Deposition of Rebecca Martinez (Mar. 23, 2004).

In the United States District Court For The District of New Jersey, Civil Action No. 02–5707 (JCL), *Ortho–McNeil Pharmaceutical, Inc.* v. *Kali Laboratories, Inc.:* Deposition of Ellen Codd (Mar. 31, 2004).

In the United States District Court For The District of New Jersey, Civil Action No. 02–5707 (JCL), *Ortho–McNeil Pharmaceutical, Inc.* v. *Kali Laboratories, Inc.:* Deposition of Laura Glauda (Mar. 5, 2004).

In the United States District Court For The District of New Jersey, Civil Action No. 02–5707 (JCL), *Ortho–McNeil Pharmaceutical, Inc.* v. *Kali Laboratories, Inc.:* Deposition of Fredrick Minn (Mar. 26, 2004).

In the United States District Court For The District of New Jersey, Civil Action No. 02–5707 (JCL), *Ortho–McNeil Pharmaceutical, Inc.* v. *Kali Laboratories, Inc.:* Deposition of Ramin Valian (Mar. 30, 2004).

In the United States District Court For The District of New Jersey, Civil Action No. 02–5707 (JCL), *Ortho–McNeil Pharmaceutical, Inc.* v. *Kali Laboratories, Inc.:* Second Expert Report of Dr. Charles E. Inturrisi (Jul. 15, 2004), 3 pages.

In the United States District Court For The District of New Jersey, Civil Action No. 02–5707 (JCL), *Ortho–McNeil Pharmaceutical, Inc.* v. *Kali Laboratories, Inc.:* Second Expert Report of Howard T. Thaler, Ph.D. (Jul. 19, 2004), [Redacted].

In the United States District Court For The District of New Jersey, Civil Action No. 02–5707 (JCL), *Ortho–McNeil Pharmaceutical, Inc.* v. *Kali Laboratories, Inc.:* Third Expert Report of Dr. Charles E. Inturrisi (Sep. 15, 2004), with attached exhibits 16 thru 19.

In the United States District Court For The District of New Jersey, Civil Action No. 02–5707 (JCL), *Ortho–McNeil Pharmaceutical, Inc.* v. *Kali Laboratories, Inc.:* Third Expert Report of Howard T. Thaler, Ph.D. (Sep. 27, 2004).

In the United States District Court For The District of New Jersey, Civil Action No. 02–5707 (JCL), *Ortho–McNeil Pharmaceutical, Inc.* v. *Kali Laboratories, Inc.:* Expert Report of Gordon Rausser, Ph.D. (Oct. 8, 2004), with attached exhibits 1 thru 10.

In the United States District Court For The District of New Jersey, Civil Action No. 02–5707 (JCL), *Ortho–McNeil Pharmaceutical, Inc.* v. *Kali Laboratories, Inc.:* Expert Report of Dr. Lee S. Simon (Oct. 6, 2004), with attached exhibits 1, 2.

In the United States District Court For The District of New Jersey, Civil Action No. 02–5707 (JCL), *Ortho–McNeil Pharmaceutical, Inc.* v. *Kali Laboratories, Inc.:* Expert Report of Gary P. Thomas, M.D. on Behalf of Defendant Kali Laboratories, (Oct. 11, 2004), with attached exhibits 1 thru 3.

In the United States District Court For The District of New Jersey, Civil Action No. 02–5707 (JCL), *Ortho–McNeil Pharmaceutical, Inc.* v. *Kali Laboratories, Inc.:* Expert Report of James Morrison on Behalf of Defendant Kali Laboratories, Part 1 of 2, and Part 2 of 2 (Sep. 22, 2004), with attached exhibits 1 thru 25.

In the United States District Court For The District of New Jersey, Civil Action No. 02–5707 (JCL), *Ortho–McNeil Pharmaceutical, Inc.* v. *Kali Laboratories, Inc.:* Expert Report of Donald R. Stanski (Jun. 15, 2004), with attached exhibits 1 thru 39 [Redacted].

In the United States District Court For The District of New Jersey, Civil Action No. 02–5707 (JCL), *Ortho–McNeil Pharmaceutical, Inc.* v. *Kali Laboratories, Inc.:* Expert Report of Eric Smith (Jun. 14, 2004), with attached exhibits 1 thru 39.

In the United States District Court For The District of New Jersey, Civil Action No. 02–5707 (JCL), *Ortho–McNeil Pharmaceutical, Inc.* v. *Kali Laboratories, Inc.:* Rebuttal Expert Report of Donald R. Stanski (Jul. 19, 2004), with attached exhibits 1 thru 34.

In the United States District Court For The District of New Jersey, Civil Action No. 02–5707 (JCL), *Ortho–McNeil Pharmaceutical, Inc.* v. *Kali Laboratories, Inc.:* Rebuttal Expert Report of Eric Smith, Ph.D. (Jul. 14, 2004), with attached exhibits 1 thru 12.

In the United States District Court For The District of New Jersey, Civil Action No. 02–5707 (JCL), *Ortho–McNeil Pharmaceutical, Inc.* v. *Kali Laboratories, Inc.:* Expert Report of Robert M. Bennett (Jul. 13, 2004), with attached exhibits 1 thru 46.

In the United States District Court For The District of New Jersey, Civil Action No. 02–5707 (JCL), *Ortho–McNeil Pharmaceutical, Inc.* v. *Kali Laboratories, Inc.:* Expert Report of Jeffrey A. Gudin, MD (Jul. 15, 2004), with attached exhibits 1 thru 33.

In the United States District Court For The District of New Jersey, Civil Action No. 02–5707 (JCL), *Ortho–McNeil Pharmaceutical, Inc.* v. *Kali Laboratories, Inc.:* Expert Report of Clark D. McKeever (Jul. 15, 2004), with attached exhibits 1 thru 17.

In the United States District Court For The District of New Jersey, Civil Action No. 02–5707 (JCL), *Ortho–McNeil Pharmaceutical, Inc.* v. *Kali Laboratories, Inc.:* Expert Report of Leslie S. Zun (Jul. 15, 2004), with attached exhibits 1 thru 24, 25 thru 46.

In the United States District Court For The District of New Jersey, Civil Action No. 02–5707 (JCL), *Ortho–McNeil Pharmaceutical, Inc.* v. *Kali Laboratories, Inc.:* Expert Report of Richard P. Rozek, Ph.D. (Jul. 19, 2004), with attached exhibits A thru Q [Redacted].

In the United States District Court For The District of New Jersey, Civil Action No. 02–5707 (JCL), *Ortho–McNeil Pharmaceutical, Inc.* v. *Kali Laboratories, Inc.:* Rebuttal Report of Michael Sofocleous (Jul. 19, 2004), with attached exhibits A thru L.

In the United States District Court For The District of New Jersey, Civil Action No. 02–5707 (JCL), *Ortho–McNeil Pharmaceutical, Inc.* v. *Kali Laboratories, Inc.:* Second Rebuttal Report of Eric Smith, Ph.D. (Oct. 8, 2004), with attached exhibits Bates Nos. ES–RR2–0001 thru ES–RR2–0011 [Redacted].

In the United States District Court For The District of New Jersey, Civil Action No. 02–5707 (JCL), *Ortho–McNeil Pharmaceutical, Inc.* v. *Kali Laboratories, Inc.:* Third Expert Report of Donald R. Stanski, M.D. (Oct. 11, 2004), with attached exhibits Bates No. DS–RR2–0001.

In the United States District Court For The District of New Jersey, Civil Action No. 02–5707 (JCL), *Ortho–McNeil Pharmaceutical, Inc.* v. *Kali Laboratories, Inc.:* Fourth Expert Report of Donald R. Stanski, M.D. (Nov. 18, 2004).

In the United States District Court For The District of New Jersey, Civil Action No. 02–5707 (JCL), *Ortho–McNeil Pharmaceutical, Inc.* v. *Kali Laboratories, Inc.:* Rebuttal Expert Report of Richard P. Rozek, Ph.D. (Nov. 19, 2004), with attached exhibits Bates Nos. OMP RR RR 0001 thru, OMP RR RR 0285.

In the United States District Court For The District of New Jersey, Civil Action No. 02–5707 (JCL), *Ortho–McNeil Pharmaceutical, Inc.* v. *Kali Laboratories, Inc.:* Expert Report of Dr. Robert M. Bennett to address new issues raised by Drs. Thomas and Simon (Nov. 18, 2004), with attached exhibits 1 thru 6.

In the United States District Court For The District of New Jersey, Civil Action No. 02–5707 (JCL), *Ortho–McNeil Pharmaceutical, Inc.* v. *Kali Laboratories, Inc.:* Fourth Expert Report of Eric Smith, Ph.D. (Nov. 17, 2004), with attached exhibits Bates Numbers ES–RR3–0001–ES–RR3–0002.

In the United States District Court For The District of New Jersey, Civil Action No. 02–5707 (JCL), *Ortho–McNeil Pharmaceutical, Inc.* v. *Kali Laboratories, Inc.:* Expert Report of Cynthia G. McCormick (Nov. 18, 2004).

In the United States District Court For The District of New Jersey, Civil Action No. 02–5707 (JCL), *Ortho–McNeil Pharmaceutical, Inc.* v. *Kali Laboratories, Inc.:* Deposition of Stephen Grond (Dec. 21, 2004).

In the United States District Court For The District of New Jersey, Civil Action No. 02–5707 (JCL), *Ortho–McNeil Pharmaceutical, Inc.* v. *Kali Laboratories, Inc.:* Deposition of Howard T. Thaler (Jan. 25, 2005) [Redacted].

In the United States District Court For The District of New Jersey, Civil Action No. 02–5707 (JCL), *Ortho–McNeil Pharmaceutical, Inc.* v. *Kali Laboratories, Inc.:* Deposition of Charles E. Inturrisi (Feb. 25, 2005).

In the United States District Court for the District of New Jersey, Civil Action No. 02–5707 (JCL), *Ortho–McNeil Pharmaceutical, Inc.* v. *Kali Laboratories, Inc.:* Deposition of Harry F. Manbeck, Jr. (Feb. 2, 2005).

In the United States District Court for the District of New Jersey, Civil Action No. 02–5707 (JCL), *Ortho–McNeil Pharmaceutical, Inc.* v. *Kali Laboratories, Inc.:* Supplemental Expert Report of Harry F. Manbeck, Jr. Oct. 11, 2004, 2 pages.

In the United States District Court For The District of New Jersey, Civil Action No. 02–5707 (JCL), *Ortho–McNeil Pharmaceutical, Inc.* v. *Kali Laboratories, Inc.:* Deposition of Gordon Rausser, Ph.D. (Jan. 14, 2005).

In the United States District Court For The District of New Jersey, Civil Action No. 02–5707 (JCL), *Ortho–McNeil Pharmaceutical, Inc.* v. *Kali Laboratories, Inc.:* Deposition of Lee S. Simon (Dec. 8, 2004).

In the United States District Court For The District of New Jersey, Civil Action No. 02–5707 (JCL), *Ortho–McNeil Pharmaceutical, Inc.* v. *Kali Laboratories, Inc.:* Deposition of Gary P. Thomas (Dec. 3, 2004).

In the United States District Court For The District of New Jersey, Civil Action No. 02–5707 (JCL), *Ortho–McNeil Pharmaceutical, Inc.* v. *Kali Laboratories, Inc.:* Deposition of James C. Morrison (Jan. 10, 2005).

In the United States District Court For The District of New Jersey, Civil Action No. 02–5707 (JCL), *Ortho–McNeil Pharmaceutical, Inc.* v. *Kali Laboratories, Inc.:* Deposition of DOnald R. Stanski, M.D. (Jan. 5, 2005) [Redacted].

In the United States District Court For The District of New Jersey, Civil Action No. 02–5707 (JCL), *Ortho–McNeil Pharmaceutical, Inc.* v. *Kali Laboratories, Inc.:* Deposition of Dr. Eric Peter Smith (Dec. 10, 2004) [Redacted].

In the United States District Court For The District of New Jersey, Civil Action No. 02–5707 (JCL), *Ortho–McNeil Pharmaceutical, Inc.* v. *Kali Laboratories, Inc.:* Deposition of Robert M. Bennett, M.D. (Jan. 12, 2005).

In the United States District Court For The District of New Jersey, Civil Action No. 02–5707 (JCL), *Ortho–McNeil Pharmaceutical, Inc.* v. *Kali Laboratories, Inc.:* Deposition of Jeffrey A. Gudin, M.D. (Jan. 7, 2005).

In the United States District Court For The District of New Jersey, Civil Action No. 02–5707 (JCL), *Ortho–McNeil Pharmaceutical, Inc.* v. *Kali Laboratories, Inc.:* Deposition of Clark D. McKeever (Nov. 11, 2004).

In the United States District Court For The District of New Jersey, Civil Action No. 02–5707 (JCL), *Ortho–McNeil Pharmaceutical, Inc.* v. *Kali Laboratories, Inc.:* Deposition of Leslie S. Zun (Nov. 9, 2004).

In the United States District Court For The District of New Jersey, Civil Action No. 02–5707 (JCL), *Ortho–McNeil Pharmaceutical, Inc.* v. *Kali Laboratories, Inc.:* Deposition of Richard P. Rozek, Ph.D. (Dec. 14, 2004).

In the United States District Court For The District of New Jersey, Civil Action No. 02–5707 (JCL), *Ortho–McNeil Pharmaceutical, Inc.* v. *Kali Laboratories, Inc.:* Deposition of Michael Sofocleous (Dec. 16, 2004).

In the United States District Court For The District of New Jersey, –, *Ortho–McNeil Pharmaceutical, Inc.* v. *Kali Laboratories, Inc.:* Deposition of Cynthia G. McCormick (Jan. 13, 2005).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals, USA, Inc.,* Complaint, (Feb. 25, 2004).

In the United States District Court for the District of New Jersey, Civil Action No. 04–886(HAA), Teva Pharmaceutical Industries LTD.'s Answer, Affirmative Defenses, Counterclaims and Demand for Jury Trail (Mar. 19, 2004), Teva Pharmaceuticals USA, Inc.'s Answer, Affirmative Defenses, and Counterclaims.

In the United States District Court for the District of New Jersey, Civil Action No:. 04–886(HAA), Teva Pharmaceutical Industries Ltd.'s Amended Answer, Affirmative Defenses, Counterclaims and Demand for Jury Trial (Oct. 26, 2004), Teva Pharmaceutical USA, Inc.'s Amended Answer, Affirmative Defenses, Counterclaims and Demand for Jury Trial (Oct. 26, 2004).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Plaintiff's Brief in Opposition to Teva's Motion for Summary Judgment of Invalidity and Noninfringement of U.S. Pat. No. 5,336,691: Claim 6 (Feb. 17, 2005) [Redacted].

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.* Rule 56.1 Statement of Undisputed Material Facts in for Defendants Teva Pharmaceutical Industries Ltd. And Teva Pharmaceutical USA, Inc.'s Motion for Summary Judgment of Invalidity and Noninfringement of U.S. Pat. No. 5,336,691: Claim 6 (Jan. 18, 2005) [Redacted].

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Brief in Support of Teva Pharmaceutical Industries Ltd. And Teva Pharmaceutical USA, Inc.'s Motion for Summary Judgment of Invalidity and Noninfringement of U.S. Patent No. 5,336, 691: Claim 6 (Jan. 18, 2005) [Redacted].

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Plaintiff's Rule 56.1 Statement of Disputed Material Facts in Opposition to Defendants Teva Ltc. And Teva USA's Motion for Summary Judgment of Invalidity and Noninfringement of U.S. Pat. No. 5,336,691: Claim 6 Feb. 17, 2005.

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Reply Brief in Further Support of Defendants' Motion for Summary Judgment of Invalidity and Noninfringement of U.S. Pat. No. 5,336,691 Claim 6, Mar. 15, 2005 (Redacted).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Declaration of William L. Warren in Support of Defendants' Motion for Summary Judgment (Jan. 18, 2005).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Teva Pharmaceuticals USA, Inc.'s Responses and Objections to Plaintiff Ortho–McNeil Pharmaceutical, Inc.'s First Set of Interrogatories [Redacted].

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Teva Pharmaceuticals USA, Inc.'s Supplemental Responses and Objections to Plaintiff Ortho–McNeil Pharmaceutical, Inc.'s First Set of Interrogatories, Nov. 29, 2004.

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Teva Pharmaceuticals USA, Inc.'s Supplemental Responses and Objections to Plaintiff Ortho–McNeil Pharmaceutical, Inc.'s First Set of Interrogatories, Dec. 10, 2004.

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Deposition of Paul Short (Nov. 22 2004).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Deposition of Robert W. Croce (Nov. 22, 2004).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Expert Report of David Schoenfeld, Ph.D. (Mar. 31, 2005).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Expert Report of Gilbert J. Fanciullo, M.D., (Mar. 17, 2005).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Expert Report of Donald R. Stanski, M.D.(Jan. 14, 2005), [Redacted].

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Expert Report of Eric Smith, Ph.D. (Jan. 14, 2005).

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Fifth Expert Report of Donald R. Stanski, M.D. (Apr. 15, 2005), with attached exhibits.

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Expert Report of J. Michael Thesz (Apr. 29, 2005), with attached exhibits.

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Expert Report of Alan Cowan (Apr. 15, 2005), with attached exhibits.

In the United States District Court for the District of New Jersey, Civil Action No. 04–886(HAA), *Ortho–McNeil Pharmaceutical, Inc.,* v. *Teva Pharmaceutical Industries Ltd., and Teva Pharmaceuticals USA, Inc.,* Fifth Expert Report of Eric Smith (Mar. 28, 2005), with attached exhibits.

Patent certification notice under Section 505(j)(2)(B)(ii) of the Federal Food, Drug, and Cosmetic Act 21 U.S.C.Section 355(j)(2(B)(ii) and 21 C.F.R. Section 314.95 from Caraco Pharmaceutical to Ortho–McNeil (Aug. 11, 2004).

In the United States District Court for the Eastern District of Michigan, *Ortho–McNeil Pharmaceutical, Inc.,* v. *Caraco Pharmaceutical Laboratories, Ltd.,* Case No. 2:04CV73698, Complaint (Sep. 22, 2004).

In the United States District Court for the Eastern District of Michigan, *Ortho–McNeil Pharmaceutical, Inc.,* v. *Caraco Pharmaceutical Laboratories, Ltd.,* Case No. 2:04CV73698, Caraco's Answer and Affirmative Defenses (Oct. 13, 2004).

In the United States District Court for the Eastern District of Michigan, *Ortho–McNeil Pharmaceutical, Inc.,* v. *Caraco Pharmaceutical Laboratories, Ltd.,* Case No. 2:04CV73698, Caraco's Response to Plaintiff's First Set of Interrogatories, (Apr. 12, 2005).

Abramowicz M., (Ed.), "Drug treatment of cancer pain," *Med. Lett. Drugs Ther.,*Oct. 29, 1982 24(621), 2 pages.

Barth H., et al., "Anaphylactoid reactions and histamine release do not occur after application of the opioid tramadol," *Agents and Actions,* 1987, 20(3/4), 310–313.

Beaver W.T., "Aspirin and Acetaminophen as Constituents of Analgesic Combinations," *Arch. Intern. Med.,* 1981, 141, 293–300.

Beaver W.T. "Combination Analgesics," *Am. J. Med.,* Sep. 10, 1984, 77(3A), 38–52.

Beaver W.T., "Impact of Non–Narcotic Oral Analgesics on Pain Management," *Am. J. Med.,* 1988, 84(suppl 5A), 3–15.

Beaver, W.T., OTC Combination Analgesics—The Issue of Efficacy, *AAS Agents and Actions Supplements,* Birkhauser Verlag, Basel, 1988, 25, 49–67.

Besel K., "Tumor–Schmerztherapie: Postskriptum [The Treatment of Tumor Pain: A Postscript]," *Münch. med. Wschr.,* 1985, 127(35), C17 (English abstract).

Beyer A., et al. "Heutige Vorstellungen zur Entstehung und Behandlung des Schmerzes [Current Understanding of the Origination and Treatment of Pain]," *Chirurg,* 1990, 61(7), 494–501 (English translation—Exhibit A).

Biscoping J., "Postoperative Schmerzbehandlung [Postoperative Pain Therapy]," *Med. Welt,* 1988, 39, 814–818 (English translation—Exhibit A).

Blaha L., "Pharmakotherapie der Schmerzzustände [Pharmacotherapy of pain]," *Med. Welt.,* 1980, 31(36), 1271–73 (English abstract).

Brinkmann J., "Analgetikatherapie bei Tumorpatienten in der Praxis [Analgetic Therapy in Tumor Patients in Practice]," *Z. Allg. Med.,* 1989, 65, 166–68 (English translation—Exhibit A).

Brown P., et al., "Tramadol Hydrochloride: Efficacy compared to codeine sulfate, acetaminophen with dextropropoxyphene and placebo in dental–extraction pain" *Eur. J. Pharmacol.,* 1990, 183, p. 1441.

Carasso R.L., et al., "The Prevention and Treatment of Migraine with an Analgesic Combination," *Br. J. Clin. Pract.,* 1984, 38, 25–27.

Chaturachinda K., et al., "A Comparative Study of Tramadol and Pethidine in Laparoscopic Interval Sterilization," *J. Med. Assn. Thai.,* 1988, 71(Suppl. 1), 55–57.

Chrubasik J., et al., "Zur Schmerzbehandlung bei Karzinompatienten [On Pain Therapy in Carcinoma Patients]," *Z. Allg. Med.,* 1986, 62, 792–797 (English translation—Exhibit A).

Coelho J.C.U., et al., "Effect of Analgesic Drugs on the Electromyographic Activity of the Gastrointestinal Tract and Sphincter of Oddi and on Biliary Pressure," *Ann. Surg.,* 1986, 204(1), 53–58.

Cooper S.A., et al., "Evaluation of oxycodone and acetaminophen in treatment of postoperative dental pain," *Oral Surg.,* 1980, 50(6), 496–501.

Cossmann M., et al., "Behandlung länger andauernder Schmerzsyndrome Beurteilung der Wirkung und Verträglichkeit von Tramadol (Tramal®) bei mehrmaliger Gabe [Treatment of Prolonged Severe Pain. Efficacy and Tolerance of Repeated Administration of Tramadol (Tramal®)]," *Münch. med. Wschr.,* 1987, 129(46), 851–854 (English abstract).

Dambacher M.A., "Therapie der Osteoporose [Therapy of osteoporosis]," *Dtsch. med. Wschr.,* 1983, 108(18), 710–713 (English abstract).

Dawson K.S., et al., "A Statistical Test for Detecting and Characterizing Departures From Additivity in Drug/Chemical Combinations," *J. Ag. Biol. Env. Stat.,* 2000, 5(3), 342–359.

De Conno F., et al., "A Clinical Study on the Use of Codeine, Oxycodone, Dextropropoxyphene, Buprenorphine, and Pentazocine in Cancer Pain," *J. Pain Sympt. Mgmt.,* 1991, 6(7), 423–427.

Derwent WPI database, accession No. 79–64031B, 1979, Abstract of JP 54–92631, 1 page.

Desjardins P.J., et al., "Efficacy of Low Dose Combination Analgesics: Acetaminophen/Codeine, Aspirin/Butalbital/Codeine, and Placebo in Oral Surgery Pain," *Anesth. Prog.,* 1986, 33(3), 143–146.

Dick W., "Schmerztherapie, eine interdisziplinäre Aufgabe (Analgetika) [Pain therapy, an interdisciplinary problem (analgesics)]," *Wien. Med. Wschr.,* 1983, 133, 7–10 (English abstract).

DiGregorio G.J., et al., "Pharmacologic Management of Pain," *Am. Fam. Phys.,* 1983, 27(5), 185–188.

Dimpfel W., et al., "Dose– and Time–Dependent Action of Morphine, Tramadol and Flupirtine as Studied by Radioelectroencephalography in the Freely Behaving Rat," *Neuropsychobiol.,* 1988, 20, 164–168.

Dionne R.A., et al., "Suppression of Postoperative Pain by Preoperative Administration of Ibuprofen in Comparison to Placebo, Acetaminophen, and Acetaminophen Plus Codeine," *J. Clin. Pharmacol.,* 1983, 23(1), 37–43.

Doenicke A., et al., "Chronische Schmerzen: Therapeutischer Beitrag der Anästhesisten [Chronic Pain: The Therapeutic Contribution of Anesthesiologists]," *Fortschritt Fortbilldung Med.,* 1980, 13(90), 263–266 (English translation—Exhibit A).

Engelhardt R., "Chemotherapie beim Bronchialkarzinom [Chemotherapy in Bronchial Carcinoma]," *Therapiewoche,* 1987, 37, 4663–4666 (English translation—Exhibit A).

Fassolt A., "Tramal® (Tramadol) zur Schmerztherapie in der postoperativen Früphase," *Schweiz. Rundschau Med. (PRAXIS),* 1980, 69, 1495–1500 (English abstract).

Felder M., et al., "Die Behandlund der Schmerzen bei Osteoporose," *Schweiz. med. Wschr.,* 1982, 112(2), 60–64 (English abstract).

Ferrer–Brechner T., et al., "Combination Therapy with Ibuprofen and Methadone for Chronic Cancer Pain," *Am. J. Med.,* 1984, 77(1A), 78–83.

Fischer M.V.,, et al., "Schmerztherapie beim Tumorpatienten [Treatment of Pain in Tumour Patients]," *Anästh. Intensivther. Notfallmed.,* 1986, 21, 78–81 (English abstract).

Flicoteaux H., et al., "Analgésie et Anesthésie "ambulatories" [Analgesia and ambulatory anesthesia]" *Conv. Méd.,* 1986, 5(4/5), 325–329 (English abstract).

Foley K.M., "The treatment of cancer pain," *New. Engl. J. Med.,* 1985, 313(2), 84–95.

Foley K.M., et al., "Analgesic Drug Therapy in Cancer Pain: Principles and Practice," *Med. Clinics N. Amer.,* 1987, 71(2), 207–232.

Forbes J.A., et al., "An evaluation of the analgesic efficacy of three opioid–analgesic combinations in postoperative oral surgery pain," *J. Oral Surg.,* 1981, 39, 108–112.

Forbes J.A., et al., "Nalbuphine, acetaminophen, and their combination in postoperative pain," *Clin. Pharmacol. Ther.,* 1984, 35(6), 843–851.

Frei F.J., et al., "Perioperative Schmerztherapie im Kindesalter: Konzepte und Realisierung," *Eur. J. Pain,* 1991, 12(1), 12–19 (English Abstract).

Freye V.E., "Opitate und Opiatantagonisten: II. Dep praktische Einstaz der Opidode [Opiates and opitae antagonists: Part 2. Practical use of opioids].," *Deutsche Apotheker Zeitung,* 1991, 131(49), 2605–2615 (English abstract).

Ganzer U., et al., "Die Schmerzbehandlung bei fortgeschrittenen Geschwülsten der Kopt–Hals–Region [Treatment of Pain in Advanced Head and Neck Cancer]," *Laryng. Rhinol. Otol.,* 1988, 67(3), 90–93 (English translation).

Gilman A. et al., eds. "Para–aminophenol derivatives," *Goodman & Gilman's The Pharmacological Basis of Therapeutics,* 6th ed., 1980, Chapter 29, 701–705.

Grond S., et al., "Tramadol—a week opioid for relief of cancer pain," *The Pain Clinic,* 1992, 5(4), 241–247.

Hackenthal E., "Therapie mit Analgetika und Antirheumatika im Alter [Therapy with analgesics and anti–rheumatic agents in the aged]," *Verh. Dtsch. Ges. Inn. Med.,* 1990, 96, 274–285 (English abstract).

Helwig B., "Analgetica," *Moderne Arzneimittel* (Stuttgart: Wissneschaftliche Verlagsgesellschaft mbH), 5th ed, 1980, 1–46.

Hempel V., et al., "Postoperative Schmerzbehandlung in der Chirurgie [Postoperative pain treatment in surgery], " *Chirurg,* 1983, 54(12), 769–774 (English translation—Exhibit A).

Hennies H.–H., et al., "Receptor Binding, Analgesic and Antitussive Potency of Tramadol and Other Selected Opioids," *Arzneim. Forsch./Drug Res.,* 1988, 38(7), 877–880.

Hinson J.A., "Reactive Metabolites of Phenacetin and Acetaminophen: A Review," *Env. Health Perspec.,* 1983, 48, 71–79.

Hotz G., et al., "Analgetika in der zahnärztlichen Praxis [Analgesics in Dental Practice]," *ZWR,* 1985, 94(11), 892–896 (English translation—Exhibit A).

Hövel M., "Knochenmatastasen—operative, orthetische und analgetische Behandlungsrichtlinien [Bone Metastases—Operative, Orthotic, and Analgetic Guidelines of Treatment]," *Orthop. Praxis,* 1989, 5/89, 284–290 (English abstract).

Huhn D., "Bedürfnisorientierte Therapie vermeidet Angst und Depression [Need–oriented therapy prevents fear and depression]," *Therapiewoche,* 1991, 41, 1918–1923 (English translation—Exhibit A).

Isele H., "Tumor–Schmerztherapie [Algotherapy in Tumour Patients]," *Münch. med. Wschr.,* 1985, 127(35), 821–823 (English abstract).

Keinänen S., "Antipyretic Therapy. Comparison of Rectal and Oral Paracetamol," *Eur. J. Clin. Pharmacol.,* 1977, 12, 77–80.

Krimmer H., et al., "Die kombinierte Infusionsanalgesie—Ein alternatives Konzept zur postoperativen Schmerztherapie [Combined infusion analgesia—an alternative concept in postoperative pain therapy]," *Chirurg,* 1986, 57(5), 327–329 (English abstract).

Lehmann K.A., "Opiate in der Kinderanaesthesie [Narcotic analgesics in pediatric anesthesia]," *Anaesthesist,* 1990, 39(4), 195–204 (English abstract).

Lierz P., et al., "Aurwachverhalten bei verschiedenen Analgosedierungsschemata [Time Course of Recovery from Different Analgesic and Sedative Therapies]," *Klin. Wochenschr.,* 1991, 69(Suppl. xxvi), 84–88 (English abstract).

Luckhaupt H., "Schmerztherapie bein Patienten mit inkurablen Kopf–Hals–Tumoren [Treatment of pain in patients with incurable head and neck tumors],"*HNO,* 1989, 11 465–468 (English translation—Exhibit A).

Luckhaupt H., "Medikamentöse Schmerztherapie bei Patienten mit fortgeschrittenen Kopf–Hals–Tumoren [Drug pain therapy in patients with advanced head–neck tumors]," *Laryng. Rhinol. Otol.,* 1990, 69, p. 663 (English abstract).

Luckhaupt H., et al., "Medikamentöse und nicht–medikamentöse Tumorchmerztherapie in der HNO–Heilkunde [Pain Therapy in Patients with Cancer of the Head and Neck]," *Laryng. Rhinol. Otol.,* 1991, 70, 683–685 (English abstract).

McQuay H.J., et al., Codeine 20 mg increases pain relief from ibuprofen 400 mg after third molar surgery. A repeat–dosing comparison of ibuprofen and an ibuprofen–codeine combination, *Pain,* 1989, 37, 7–13.

Mehlisch D.R., et al., "Tramadol hydrochloride: efficacy compared to codeine sulfate, acetaminophen with dextropropoxyphene and placebo in dental–extraction," *Pain Suppl.,* 1990, 5, p. S41, Abstract No. 76.

Meier P.J., et al., "Medikamentöse Schmerztherapie Medicinal Pain Therapy," *Therapeut. Umschau,* 1989, 48(8), 526–536 (English translation—Exhibit A).

*Merck Index,* 11th ed. 1989, pp. 8 and 1506. Acetaminophen (No. 49) and Tramadol (No. 9485).

Mikić, B., et al., "Klinicko Ispitivanje Analgetika >>Tramadol<< u olbiku za oralnu upotrieu [Clinical investigation of the Analgetic "Tramadol" in the form for oral use]," *Acta orthop. Iugosl.,* 1985, 16(3), 93–96 (English translation—Exhibit A).

Montéfiore A., et al., "Comparaison du Tramadol a l'association dextropropoxyphene + paracetamol dans le traitement de la douleur post–operatorie," *Thérapie,* 1991, 46, 491–495, Abstract No. 15 (English abstract).

Morant R., et al., "Pharmakokinetische Einflüsse auf die Morphintoxizität mit Fallbeispielen [Pharmacokinetic Influences on Morphine Toxicity with Case Studies]," *Schweiz. Rundschau Med.* (*praxis*), 1991, 80(26), 719–722 (English translation—Exhibit A).

Müller H. et al., "Hämodynamische und respiratorische Effekte von Tramadol bei Lachgas–Sauerstoff–Beatmung und in der postoperativen Phase [Effects of Tramadol on Haemodynamics and Respiration During $N_2O$—$O_2$ Ventilation and in the Postoperative Period]," *Anaesthesist,* 1982, 31, 604–610 (English abstract).

Müller–Plettenberg D., "Chronische Schmerzzustände—Infektiöse Darmerkrankungen—Harnwegsinfekte [Chronic Pain Conditions—Infectious Intestinal Diseases—Urinary Tract Infections]," *Braun Therapiewoche,* 1984, 34(11), 1685–1687 (English translation—Exhibit A).

Nickel B., "The antinociceptive activity of flupirtine: a structurally new analgesic," *Postgrad. Med. J.,* 1987, 63, 19–28.

Padmasuta K., "Effects of Tramadol on postoperative wound pain in Thai patients," *Curr. Ther. Res.,* 1985, 38(2), 316–320.

Padmasuta P., et al., "The Efficacy of Tramadol in the Interval Laparoscopic Sterilization: A Comparison of Two Dosage Regimen," *J. Med. Assn. Thai.,* 1988, 71(Suppl. 2), 61–63.

Peikert V.A., et al., "Systemische Pharmakotherapie bei Kruezschmerz [Systemic Drug Therapy of Low Back Pain—Indications and Practical Application]," *Fortschr. Med.,* 1989, 107(18), 403–405 (English abstract).

Polák J., et al., "Terapie Nadorove bolesti [Tumour Pain Therapy]," *Sborn. lek.,* 1988, 90(11–12), 358–363 (English translation—Exhibit A).

Porges P., "Moderne Trends in der Krebsscherztherapie [Modern trends in cancer pain therapy]," *Arch. Geschwulstforsch.,* 1991, 61(1), 17–21 (English translation).

Preston K.L., et al., "Effects of Tramadol in Humans: Assessment of its Abuse Potential," *Natl. Inst. Drug Abuse Res. Mono. Ser.,* 1989, 95, p. 392.

Preston K.L., et al. "Abuse potential and pharmacological comparison of tramadol and morphine," *Drug Alc. Depend.,* 1991, 37, 7–17.

Richter W., et al., "Clinical Investigation on the Development of Dependence during Oral Therapy with Tramadol, "*Arzneim. Forsch./Drug Res.,* 1985, 35(11), 1742–1744.

Schlunk T., et al., "Schmerz und Schmerztherapie bei Tumorpatienten [Pain and Pain Therapy for Tumor Patients]," *Med. Welt.,* 1990, 41, 297–303 (English translation—Exhibit A).

Schönhöfer P.S. "Möglichkeiten und Grenzen einer pharmakologischen Beeinglussung der Muskulatur [Capabilities and Limits of Pharmacological Manipulation of the Musculature]," *Verb. Dtsch. Ges. Rheumatol.,* 1981, 7, 49–52 (English translation—Exhibit A).

Schoon W., et al., "Grundlagen der Pharmakotherapie tumorinduzierter Schmerzsyndrome [Fundamentals of Pharmacotherapy of Tumor–Induced Pain Syndrome]," *Med. Klin.,* 1987, 82(23), 824–831 (English translation—Exhibit A).

Seitz W., "Endokrine Reaktionsmuster im Verlauf der rinphasigen Tramadol–$N_2O$–Kombinationsnarkose [Effects of Tramadol–$N_2O$–Anaesthesia and Surgery on the Endocrine System]," *Anästh. Intensivther. Notfallmed.,* 1982, 17, 325–331 (English abstract).

Senn H.J., "Das Schmerzproblem in de Onkologie [The problem of pain in oncology]," *Schweiz. med. Wschr.,* 1990, 120(31/32), 1135–1142 (English translation—Exhibit A).

Sonne J., et al., "Therapeutic Doses of Codeine Have no Effect on Acetaminophen Clearance or Metabolism," *Eur. J. Clin. Pharmacol.,* 1988, 35, 109–111.

Sorge J., et al., "Schmerztherapie bein gynäkologischen Malignomen [Pain Therapy in Patients with Gynaecological Cancer]," *Geburtsh. u. Frauenheik.,* 1990, 50(2), 93–100 (English translation—Exhibit A).

Stacher G., et al., "Effects of tolmetin, paracetamol, and of two combinations of tolmetin and paracetamol as compared to placebo on experimentally induced pain. A double blind study," *Int. J. Clin. Pharmacol. Biopharm.,* 1979, 17(6), 250–255.

Staehler G., "Die Harnleiterkolik [Renal Colic]," *Internist,* 1989, 30, 110–113 (English abstract).

Staritz M., et al., "Electromagnetically generated extracorporeal shockwaves for fragmentation of extra– and intrahepatic bile duct stones: indications, success and problems during a 15 months clinical experience," *Gut,* 190, 31, 222–225.

Strumpf M., et al., "Schmerztherapie bei Lungentumoren [Lung Cancer Pain Therapy]," *Atemw.–Lungenkrkh.,* 1989, 15(3), 111–115 (English translation—Exhibit A).

Sunshine A., et al., "Analgesic oral efficacy of tramadol hydrochloride in postoperative pain," *Clin. Pharmacol. Ther.,* 1992, 51(6), 740–746.

Suvonnakote T., et al., "Pain Relief During Labour," *J. Med. Assn. Thai.,* 1986 69(11), 575–580.

Sveen K., et al., "Paracetamol/codeine in relieving pain following removal of impacted mandibular third molars," *Int. J. Oral Surg.,* 1975, 4, 258–266.

Takeda F. "Results of field–testing in Japan of the WHO Draft Interim Guideline on Relief of Cancer Pain," *The Pain Clinic,* 1986, 1(2), 83–89.

Tallarida R.J., et al., ". Minireview—Statistical analysis of drug–drug and site–site interactions with isobolograms," *Life Sci.,* 1989, 45(11), 947–961.

Tallarida R.J., et al., "Testing for synergism over a range of fixed ration drug combinations: replacing the isobologram," *Life Sci.*, 1996, 58(2), PL23–PL28.

Tallarida R.J., "Analysis of Drug Combinations Over a Range of Drug Ratios," *Drug Synergism and Dose–Effect Data Analysis,* Chapman & Hall/CRC, Boca Raton, 2000, Chapter 7, 123–129.

Terrahe K., et al., "Welche Analgetika empfehlen Sie nach der Tonsillektomie? [Which analgesics do you recommend following tonsillectomy?]," *Laryng. Rhinol. Otol.,* 1989, 68, p. 189, (English abstract).

Tigges F.–J., "Schmerzmittel bei Tumorerkrankungen [Analgesics in malignant disease]," *Therapiewoche,* 1984, 34(24), 3713–3716 (English abstract).

Wang K.Y., "[Tramadol Fentanyl WSWL (Extracorporeal Shock Wave Lithotripsy)]," *Anaesth. Sinica,* 1989, 27, 341–347 (English abstract).

Weber E., "Chirurgisch relevante Nebenwirkungen von Medikamenten: Analgetica [Surgery–related adverse effects drugs: analgesics].," *Chirurg,* 1981, 52(2), 76–80 (English abstract).

World Health Organization, *Cancer Pain Relief,* Geneva, 1986, 7–74.

Wörz R., "Control of Cancer Pain with Analgesics Acting in the Central Nervous System," *Recent Results Cancer Res.,* 1984, 89, 100–106.
Wörz R., et al., "Medikamentoöse Therapie von Karzinomschmerzen [Medical Therapy of Cancer Pain]," *Med. Mo. Pharm.,* 1985, 8(10), 292–300 (English translation—Exhibit A).
Yanagita T. "Drug Dependence Potential of 1–(m–Methoxyphenyl)–2–(dimethylaminomethyl)–cyclohexan–1–ol Hydrochoride (Tramadol) Tested in Monkeys," *Arzneim. Forsch./Drug Res.,* 1978, 28(1), 158–163.
Young R.E.S., "A comparison of analgesic effectiveness of oral butorphanol/acetaminophen, oxycodone/acetaminophen and placebo in hospitalized postsurgical patients," *J. Med.,* 1979, 10(6), 417–428.
Zech D., "Medikamentöse Tumorschmerztherapie nach mem WHO–Stufenplan [Drug–based Tumor Pain Therapy in Accordance with the WHO Step–wise Plan]," *Dtsch. Z. Onkologie,* 1991, 23, 85–92 (English translation—Exhibit A).
Austrian Patent Office search report in related application AT 9605733–6, dated Mar. 15, 1999.
Japanese Patent Office examiner's action in related applicaton JP 505447/93, dated Oct. 2, 2001 (English translation).
Memorandum to G. Tutwiler from N. Landekic, Revised Tramadol [Business Opportunity] Analysis, with attachments, dated Aug. 19, 1988 (in redacted form as produced in litigation).
*Ortho–McNeil Pharmaceutical, Inc.* v. *Kali Laboratories, Inc.,* No. CV–02–5707 (JCL) (D.N.J.), Complaint, Nov. 25, 2002.
*Ortho–McNeil Pharmaceutical, Inc.* v. *Kali Laboratories, Inc.,* No. CV–02–5707 (JCL) (D.N.J.), Defendant's Answer and Counterclaim, Jan. 2, 2003.
*Ortho–McNeil Pharmaceutical, Inc.* v. *Kali Laboratories, Inc.,* No. CV–02–5707 (JCL) (D.N.J.), Deposition of Robert B. Raffa, Nov. 25, 2003.
*Ortho–McNeil Pharmaceutical, Inc.* v. *Kali Laboratories, Inc.,* No. CV–02–5707 (JCL) (D.N.J.), Deposition of Jeffry L. Vaught, Jan. 8, 2004.
Patent certification notice under FFDCA § 505(j)(2)(B)(ii) from Kali Laboratories to Ortho–McNeil Pharmaceuticals, dated Oct. 17, 2002.
Patent certification notice under FFDCA § 505(j)(2)(B)(ii) from Teva Pharmaceuticals USA to Ortho–McNeil Pharmaceuticals, dated Jan. 22, 2004.
R.W. Johnson Pharmaceutical Research Institute, Abbreviated Final Clinical Study Report, Tramadol Hydrochloride with Acetaminophen in Pain of Cesarean Section (Protocol CB), dated Apr. 13, 1994.
R.W. Johnson Pharmaceutical Research Institute, Abbreviated Final Clinical Study Report, Tramadol Hydrochloride with Acetaminophen: Factorial Efficacy in Dental–Extraction Pain (Protocol CA), dated Jun. 23, 1994.
R.W. Johnson Pharmaceutical Research Institute, Protocol CA—Phase II: Tramadol Hydrochloride with Acetaminophen: Factorial Efficacy in Dental–Extraction Pain (Protocol CA), dated Nov. 21, 1989; with appended executed agreement signature page.
R.W. Johnson Pharmaceutical Research Institute, Protocol CB—Phase II: Tramadol Hydrochloride with Acetaminophen in Pain of Cesarean Section, dated Oct. 29, 1990.
FDA, Prescription and Over–the–Counter Products Containing Phenacetin, Federal Register, 47 FR 34636 (1982).
Hardman et al., Goodman and Gilman's The Pharamacological Basis of Therapeutics, 5$^{th}$ Ed., p. 656–659 (1990).
Letter from Kurt Nielsen, Ph.D., to Ortho–McNeil Pharmaceutical, Inc., Re:. *Patent Certification Notice—U.S. Pat No. 5,336,691, Tramadol/Acetaminophen Tablets, 37.5 m/325 mg, Teva Pharmaceutical USA, Inc., 's ANDA* 76–914, Jan. 22, 2004, 12 pages.
*Ortho–McNeil Pharmaceutical, Inc.* v. *Kali Laboratories, Inc.,* No. CV–02–5707(JCL) (D.N.J.), Kali's Supplemental Response to Ortho–McNeil's First Set of Interrogatories, May 7, 2004.
*Ortho–McNeil Pharmaceutical, Inc.* v. *Kali Laboratories, Inc.,* No. CV–02–5707(JCL) (D.N.J.), Kali's Supplemental Response to Ortho–McNeil's Second Set of Interrogatories, May 7, 2004.
*Ortho–McNeil Pharmaceutical, Inc.* v. *Kali Laboratories, Inc.,* No. CV–02–5707(JCL) (D.N.J.), Kali's Supplemental Response to Ortho–McNeil's Third Set of Interrogatories, May 7, 2004.
Expert Report of Dr. Stefan Grond, with Attached Exhibits 1 thru 9, May 26, 2004.
*Ortho–McNeil Pharmaceutical, Inc.* v. *Kali Laboratories, Inc.,* No. CV–02–5707(JCL) (D.N.J.), Declaration of Deirdre A. Clarkin, with Attached Exhibts 1 thru 18, May 27, 2004.
*Ortho–McNeil Pharmaceutical, Inc.* v. *Kali Laboratories, Inc.,* No. CV–02–5707(JCL) (D.N.J.), Declaration of Pearl T.L. Siew, with Attached Exhibits 1 thru 12, May 28, 2004.
*Ortho–McNeil Pharmaceutical, Inc.* v. *Kali Laboratories, Inc.,* No. CV–02–5707(JCL) (D.N.J.), Declaration of Daniel G. Brown, with Attached Exhibits 1 thru 23, May 28, 2004.
*Ortho–McNeil Pharmaceutical, Inc.* v. *Kali Laboratories, Inc.,* No. CV–02–5707(JCL) (D.N.J.), Rule 56.1 Statement of Undisputed Material Facts for Defendant Kali Laboratories' Motion for Summary Judgment of Invalidity and Noninfringement of U.S. Pat. No. 5,336,691: Claim 6, May 28, 2004, 12 pages.
*Ortho–McNeil Pharmaceutical, Inc.* v. *Kali Laboratories, Inc.,* No. CV–02–5707(JCL) (D.N.J.), Brief in Support of Defendant Kali Laboratories' Motion for Summary Judgment of Invalidity and Noninfringement of U.S. Pat. No. 5,336,691: Claim 6, May 28, 2004, 30 pages.
*Ortho–McNeil Pharmaceutical, Inc.* v. *Kali Laboratories, Inc.,* No. CV–02–5707(JCL) (D.N.J.), Brief in Support of Defendant Kali's Motion for Summary Judgment of Invalidity Under the 35 U.S.C. § 102(b) Public–Use Bar, May 28, 2004, 16 pages.
Expert Report of Howard T. Thaler, Ph.D., with Attached Exhibits 1 thru 7, Jun. 14, 2004.
*Ortho–McNeil Pharmaceutical, Inc.* v. *Kali Laboratories, Inc.,* No. CV–02–5707(JCL) (D.N.J.), Defendant's Expert Report of Harry F. Manbeck, Jr. Under R.26(a)(2)(B) of the Federal Rules of Civil Procedure, with Attached Exhibits 1 thru 9, Jun. 14, 2004.
Expert Report of Charles E. Inturrisi, Ph.D., with Attached Exhibits 1 thru 15, Jun. 15, 2004.
In the United States District Court for the Eastern District of Michigan, *Ortho–McNeil Pharmaceutical, Inc.,* Plaintiff, v. *Caraco Pharmaceutical Laboratories, Ltd.,* Defendant., Case No: 04–CV–73698, Caraco's Reply Brief in Support of its Motion for Summary Judgement of Non–Infringement, Sep. 7, 2005.

In the United States District Court for the Eastern District of Michigan, Southern Division, *Ortho–McNeil Pharmaceutical, Inc.,* Plaintiff, v. *Caraco Pharmaceutical Laboratories, Ltd.,* Defendent., Case No: 04–CV–73698, Opinion and Order Granting Defendent's Motion for Summary Judgement of Non–Infringement, Oct. 19, 2005, 11 pages.

In the United States District Court for the Eastern District of Michigan, Southern Division, *Ortho–McNeil Pharmaceutical, Inc.,* Plaintiff, v. *Caraco Pharmaceutical Laboratories, Ltd.,* Defendent., Case No: 04–CV–73698, Judgement, Oct. 19, 2005, 1 page.

* cited by examiner

FIG I
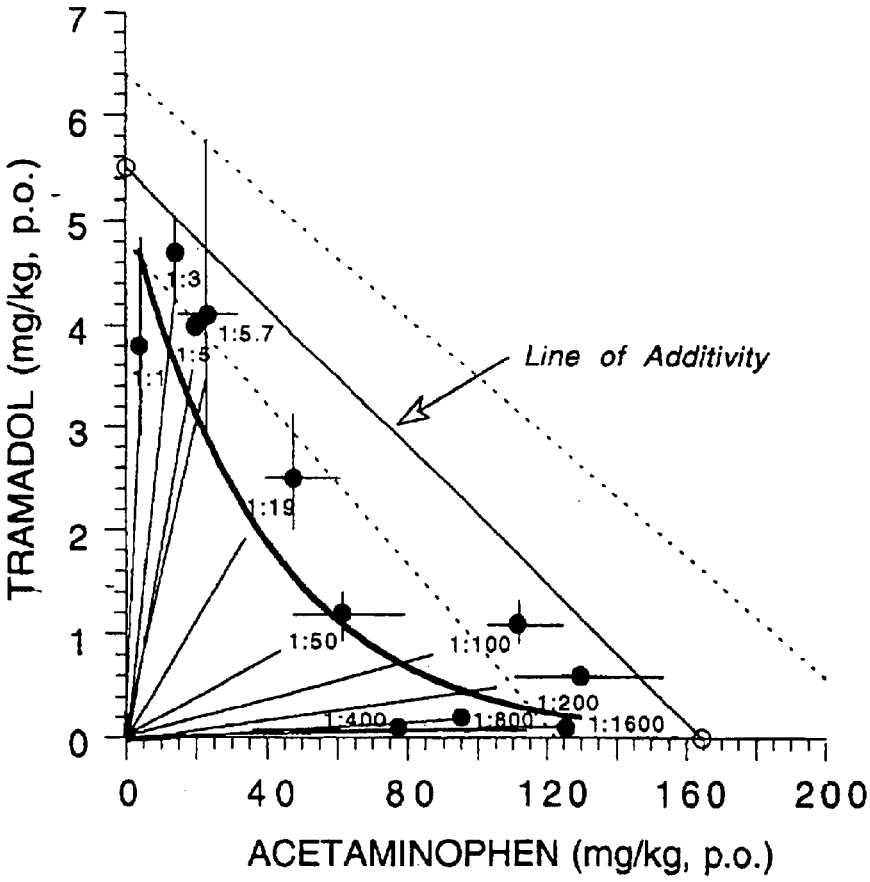

COMPOSITION COMPRISING A TRAMADOL MATERIAL AND ACETAMINOPHEN AND ITS USE

Matter enclosed in heavy brackets [ ] appears in the original patent but forms no part of this reissue specification; matter printed in italics indicates the additions made by reissue.

CROSS REFERENCE

This case is related to application Ser. Nos. 7/759,259, filed Sep. 13, 1991, now U.S. Pat. No. 5,223,541 and 07/785,137, filed Oct. 30, 1991, now abandoned, and is a continuation-in-part of application serial No. 07/755,924, filed Sep. 6, 1991, now abandoned. Claims priority, application Germany, filed Apr. 2, 1963, C29547 IV b/12o and application Germany, filed Apr. 2, 1963, C29548 IVd/12p.

BACKGROUND OF THE INVENTION

U.S. Pat. No. 3,652,589 discloses a class of analgesic cycloalkanol-substituted phenol esters having a basic amine group in the cycloalkyl ring. The compound (1RS, 2RS)-[(dimethylamino)-methyl]-1-(3-methoxy-phenyl) cyclohexanol, commonly known as tramadol, is specifically disclosed therein. A series of articles pertaining to the pharmacology, toxicology and clinical studies of tramadol are found in Arzneim. Forsch, (Drug Res.), 28(I), 114(1978). Driessen et al., Arch. Pharmacol., 341, R104 (1990) disclose that tramadol produces its analgesic effect through a mechanism that is neither fully opioid-like or non-opioid-like. The Abstracts of the VI th World Congress on Pain, Apr. 1–6 (1990), disclose that tramadol hydrochloride is an orally active pure agonist opioid analgesic. However, clinical experience indicates that tramadol lacks many of the typical side effects of opioid agonists, e.g., respiratory depression (W.-Vogel et al., Arzneim. Forsch. (Drug Res.), 28(I), 183 (1978)), constipation (I. Arend et al., Arzneim. Forsch, (Drug Res.), 28(I), 199 (1978)), tolerance (L. Flohe et, al., Arzeim. Forsch, (Drug Res.), 28(I), 213 (1978)), and abuse liability (T. Yanagita, Arzneim. Forsch, (Drug Res.), 28(I), 158 (1978)). When given at a dose of 50 mg by rapid i.v. injection, tramadol may produce certain side effects unique to tramadol including hot flushes and sweating. Despite these side effects, tramadol's combination of non-opioid and opioid activity makes tramadol a very unique drug. Tramadol is currently being marketed by Grunenthal GMBH as an analgesic.

Opioids have for many years been used as analgesics to treat severe pain. They, however, produce undesirable side effects and as a result cannot be given repeatedly or at high doses. The side effect problems are well documented in the literature. See, for example, J. Jaffe and W. Martin in chapter 15, "The Pharmacological Basis of Therapeutics", editors L. Goodman and A. Gilman, 5th Edition, 245 (1975) wherein it is disclosed that morphine and its congeners, e.g., codeine, hydrocodone and oxycodone, are opioid agonist analgesics that exhibit side effects such as respiratory depression, constipation, tolerance and abuse liability.

As alternatives to using opioids, non-opioids such as acetaminophen (APAP) and aspirin are used as analgesics. APAP, like aspirin, is not subject to the tolerance, addiction and toxicity of the opioid analgesics. However, APAP and aspirin are only useful in relieving pain of moderate intensity, whereas the opioid analgesics are useful in relieving more intense pain; See Woodbury, D. and Fingl, E. in "The Pharmacological Basis of Therapeutics", 5th Ed.; Goodman, L. and Gilman, A., Chapter 15, pages 325 (1975).

To reduce the side effect problems of opioids, opioids have been combined with other drugs including non-opioid analgesic agents, which lowers the amount of opioid needed to produce an equivalent degree of analgesic. It has been claimed that some of these combination products also have the advantage of producing a synergistic analgesic effect. For example, A. Takemori, Annals New York Acad. Sci., 281, 262 (1976) discloses that compositions including combinations of opioid analgesics with drugs other than analgesics exhibit a variety of effects, i.e., subadditive (inhibitory), additive or superadditive. R. Taber et al., J. Pharm. Expt. Thera., 169(1), 29 (1969) disclose that the combination of morphine and methadone, another opioid analgesic, exhibits an additive effect. U.S. Pat. No. 4,571, 400 discloses that the combination of dihydrocodeine, an opioid analgesic, and ibuprofen, a non-opioid analgesic, provides super-additive effects when the components are within certain ratios. A. Pircio et al., Arch. Int. Pharmacodyn., 235, 116 (1978) report superadditive analgesia with a 1:125 mixture of butorphanol, another opioid analgesic, and acetaminophen (APAP), a non-opioid analgesic, whereas a 1:10 mixture did not show any statistically significant superadditive analgesia.

Combinations of non-opioid analgesics have also been prepared to avoid the side effects associated with opioids, and the combinations are noted to have the benefit of requiring less of each ingredient and in producing superadditive effects. G. Stacher et. al., Int. J. Clin. Pharmacol. Biopharmacy, 17, 250 (1979) report that the combination of non-opioid analgesics, i.e., tolmetin and APAP, allows for a marked reduction in the amount of tolmetin required to produce analgesia. In addition, U.S. Pat. No. 4,260,629 discloses that an orally administered composition of APAP and zomepirac, a non-opioid analgesic, in a particular weight ratio range produces a superadditive relief of pain in mammals. Furthermore, U.S. Pat. No. 4,132,788 discloses that 5-aroyl-1-(lower)alkylpyrrole-2-acetic acid derivatives, non-opioid analgesics, when combined with APAP or aspirin exhibit superadditive antiarthritic activity. However, there have been warnings against the daily consumption of non-opioid analgesic mixtures and of the consumption of a single non-opioid analgesic in large amounts or over long periods (see, D. Woodbury and E. Fingl at page 349).

The prior art, however, does not disclose that tramadol an 'atypical' opioid analgesic, can or should be combined with another analgesic to lessen the side effects of each or to yield a composition comprising a tramadol material and another analgesic that exhibits superadditive analgesia.

SUMMARY OF THE INVENTION

It has now been found that a tramadol material which includes various forms of tramadol as defined hereinafter can be combined with APAP to produce analgesia. The combination employs lesser amounts of both the tramadol material and APAP than would be necessary to produce the same amount of analgesia if either was used alone. By using lesser amounts of both drugs the side effects associated with each are reduced in number and degree. Surprisingly, the compositions comprising the tramadol material and APAP have been found to exhibit synergistic analgesic effects when combined in certain ratios. The compositions according to this invention may also be useful in treating tussive conditions.

BRIEF DESCRIPTION OF THE DRAWING

FIG. 1 is an isobologram showing the analgesic effect of tramadol hydrochloride and acetaminophen composition on the acetylcholine-induced abdominal constriction in mice.

DETAILED DESCRIPTION OF THE INVENTION

The present invention is directed to compositions comprising a tramadol material and acetaminophen. The tramadol material is any one of (1R, 2R or 1S, 2S)-(dimethylaminomethyl)-1-(3-methoxyphenyl)-cyclohexanol (tramadol), its N-oxide derivative ("tramadol N-oxide"), and its O-desmethyl derivative ("O-desmethyl tramadol") or mixtures thereof. It also includes the individual stereoisomers, mixtures of stereoisomers, including the racemates, pharmaceutically acceptable salts of the amines, such as the hydrochloride salts, solvates and polymorphs of the tramadol material. Tramadol is commercially available from Grunenthal or may be made by the process described in U.S. Pat. No. 3,652,589, which is herein incorporated by reference.

Tramadol N-oxide is prepared by treating tramadol as a free base with an oxidizing agent, e.g., hydrogen peroxide (30%), in an organic solvent, e.g., methanol or isopropanol, with, bit preferably without heating. See, "Reagents For Organic Synthesis", 1, 471, Fieser & Fieser eds. Wiley N.Y.; (1987), B. Kelentey et al., Arzneim, Forsch., 7, 594 (1957). With heating, the reaction takes about 1 hour, whereas without heating the reaction takes about 3 days. Following the oxidation, the mixture is treated with an agent, e.g. $PtO_2$ or preferably Pt/C, for about a day, to destroy the excess hydrogen peroxide. The mixture is filtered, followed by the evaporation of the filtrate and then the residue is recrystallized from an organic solvent mixture, e.g., methylene chloride/ethyl acetate.

O-Desmethyl tramadol is prepared by treating tramadol as a free base under O-desmethylating reaction conditions, e.g., reacting it with a strong base such as NaH or KH, thiophenol and diethylene glycol (DEG) with heating to reflux. See, Wildes et al., J. Org. Chem., 36, 721 (1971). The reaction takes about an hour, followed by the cooling and then quenching in water of the reaction mixture. The quenched mixture if acidified, extracted with an organic solvent such as ethyl ether, basified and then extracted with a halogenated organic solvent such as methylene chloride. The extract is then dried and the solvent evaporated to yield the O-desmethyl product, which may then be short-path distilled, converted to its corresponding salt, e.g., treated with an acidified (HCl/ethanol) solution, and recrystallized from an organic solvent mixture, e.g., ethanol/ethyl ether.

The pharmacology of acetaminophen is reviewed by B. Ameer et al., Ann. Int. Med., 87, 202 (1977), and the preparation of acetaminophen is disclosed in U.S. Pat. No. 2,998,450, which is incorporated herein by reference.

The APAP and the tramadol material are generally present in a weight ratio of tramadol material to APAP from about 1:1 to 1:1600. Certain ratios result in a composition which exhibits synergistic analgesic effects. For example, in a composition comprising a tramadol material and APAP, the ratio of the tramadol material: APAP is preferably from about 1:5 to 1:1600; and, more preferably, from about 1:19 to 1:800.

The most preferred ratios are from about 1:19 to 1:50. Compositions of a tramadol material and APAP within these weight ratios have been shown to exhibit synergistic analgesic effects. In addition, the particular compositions wherein the ratio of the components are about 1:1 and about 1:5 are encompassed by the present invention.

The tramadol/APAP formulations according to the present invention may also contain therapeutically effective amounts of one or more other pharmaceutical actives including but not limited to decongestants or bronchodilators (such as pseudoephedrine, phenylpropanolamine, phenylephrine and pharmaceutically acceptable salts thereof), antitussives (such as caraminophen, dextromethorphan and pharmaceutically acceptable salts thereof) antihistamines (such as chlorpheniramine, brompheniramine, dexchlorpheniramine, dexbromphreniramine, triprolidine, doxylamine, tripelennamine, cyproheptadine, hydroxyzine, pyrilamine, azatadine, promethazine and pharmaceutically acceptable salts thereof), non-sedating antihistamines (such as acrivastine, astemizole, cetirizine, ketotifen, loratidine, temelastine, terfenadine (including the metabolites disclosed in U.S. Pat. No. 4,254,129 and 4,284,957 hereby incorporated by reference) and pharmaceutically acceptable salts thereof), muscle relaxants (such as glycerylmonether SMRS, methocarbamol, mephenesin, mephenesin carbamate, mephenesin acid succinate, cyclobenzaprine, chlorphenesin carbamate, chlorzoxazone or pharmceutically acceptable salts thereof) and suspected adjuvants (such as diphenhyhdramine, caffeine, xanthine derivatives (including those disclosed in U.S. Pat. No. 4,558,051, hereby incorporated by reference) and pharmaceutically acceptable salts thereof) and combinations of any of the aforesaid pharmaceuticals. The aforesaid pharmaceuticals may be combined with a tramadol/acetaminophen formulation for the treatment of such ailments as allergies, sleep disorders, cough, colds, cold-like and/or flu symptoms in mammals including humans.

Pharmaceutical compositions comprising the tramadol material and acetaminophen and when desired other pharmaceutical actives in an intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in an oral dosage form, any of the usual pharmaceutical media may be employed. For example, in the case of oral liquid preparations (such as suspensions, elixirs and solution), water, glycols, oils, alcohols, flavoring agents, preservatives, coloring agents and the like may be used. In the case of oral solid preparations (such as, for example, powders, capsules an tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, containing from 0.1 to about 800 mg/kg, and preferably from about 0.3 to 200 mg/kg of the active ingredients. The dosage unit is calculated based on the amount of active which may be given to a 70 kg human subject in a single dose. The pharmaceutical compositions may be given at a daily dosage of from about 10 to 6000 mg/kg/day. However, it will be appreciated that the precise dose of the active ingredients will vary depending upon the relative amounts of active components being used. In the case wherein one or more other pharmaceutical components are added to the tramadol/APAP composition those components may be added in amounts known in the art and may be given at dosages conventional for such components. For example, decongestants and bronchodilators may be given in a single dosage of from about 12.5 to 75 mg/kg and at a daily dosage of from about 60 to 150 mg/kg/day. Antitussives may be given in a single dosage of from about 2.5 to 30 mg/kg and at a daily dosage of from about 20 to 120 mg/kg/day. Antihistamines may be given in a single dosage of from about 1 to 50 mg/kg and at a daily dosage of from about 4 to 600 mg/kg/day. Non-sedating antihistamines may be given in a single 1 dosage of from about 8 to 30 mg/kg and at a daily dosage of from about 30 to 120 mg/kg/day. Muscle relaxants may be given at a single dosage of from about 10 to 1500 mg/kg and at a daily dosage of from about 60 to 8000 mg/kg/day. Adjuvants may be given in a single dosage of from about 1 to 25 mg/kg and at a daily dosage of from about 1 to 100 mg/kg/day.

The following experimental examples describe the invention in greater particularly and are intended to be a way of illustrating but not limiting the invention.

EXAMPLE 1

Preparation of the Combined Doses of Tramadol and APAP

The preparation of different ratios of a tramadol/APAP combination is effected by first preparing a stock solution of tramadol having a concentration expressed in $mg_{drugs}$ per 10 mL of distilled water. For example, 8 mg of tramadol as the free base is dissolved per 10 mL of water to yield the highest dose of tramadol stock solution. The stock solution of the tramadol is then diluted with a sufficient amount of distilled water to prepare the lower doses of the tramadol per 10 mL of distilled water. The combinations are then made by adding 10 mL of each dilution to the appropriate mg of APAP to achieve the desired ratio of tramadol to APAP. For the 1:50 example: 400 mg of APAP as the free base is suspended with 10 mL of the 8 mg tramadol solution and 2 drops of TWEEN 80, a pharmacological dispersant, manufactured by Fisher Scientific Company, to yield the 1:50 ratio, i.e. (8 mg:400 mg) combination per 10 mL of water. Each ratio was prepared separately in a similar manner and injected in a volume of 10 mL/kg per mouse.

EXAMPLE 2

Preparation of the Combined Doses of Tramadol N-oxide and APAP

First, tramadol N-oxide was prepared as set forth hereinafter. Tramadol hydrochloride (0.5 mol) was converted to its free base in basified water (pH>9) and then extracted with ether. The ether was evaporated to yield the crystalline hydrate of tramadol. The solid was then heated with steam under a high vacuum to remove as much water as possible to yield 131.5 g of material. The material was dissolved in methanol (500 mL) and 65 g of 30% $H_2O_2$ was added. The solution was stirred for 3 hours and then an additional 65 g of the 30% $H_2O_2$ was added. The reaction was stirred for 2.5 days at room temperature. Approximately 10 mg of $PtO_2$ on carbon (use of Pt/C is suggested for its ease of removal) was added to the reaction mixture, and very gentle foaming took place. An additional 10 mg of $PtO_2$ was added and the reaction mixture was stirred overnight and then filtered thru a filter aid. The filtrate was concentrated under vacuum while being heated to a temperature of <40° C. The residue was taken up in methylene chloride. Since the methylene chloride solution contained some colloidial platinum, the solution was diluted with ethyl acetate to 1 L and filtered through a nylon filter membrane (0.45μ pore size) to yield a clear colorless filtrate. The filtrate was concentrated to 600 mL, and then ethyl acetate was added continuously to maintain a volume of 800 mL while the solution was heated until a vapor temperature of 74° C. was reached. The solution was then cooled to room temperature. The solid was collected by filtration, washed with ethyl acetate and dried in vacuo to yield 126.6 g of the tramadol N-oxide (mp. 159.5°–160° C.).

C16H25NO3 Theor.: C, 68.78; H, 9.27; N, 5.01 Found: C, 68.65; H, 9.22; N, 4.99

The preparation of different ratios of a tramadol N-oxide/APAP combination is effected by first preparing a stock solution of tramadol-N-oxide having a concentration expressed in $mg_{drugs}$ per 10 mL of distilled water. For example, 8 mg of tramadol N-oxide as the free base is dissolved per 10 mL of water to yield the highest dose of tramadol stock solution. The stock solution of the tramadol-N-oxide is then diluted with a sufficient amount of distilled water to prepare the lower doses of the tramadol N-oxide per 10 mL of distilled water. The combinations are then made by adding 10 mL of each dilution to the appropriate mg of APAP to achieve the desired ratio of tramadol N-oxide to APAP. For the 1:50 example: 400 mg of APAP as the free base is suspended with 10 mL of the 8 mg tramadol N-oxide solution and 2 drops of TWEEN 80, a pharmacological dispersant, manufactured by Fisher Scientific Company, to yield the 1:50 ratio, i.e., (8 mg:400 mg) combination per 10 mL of water. Each ratio was prepared separately in a similar manner and injected in a volume of 10 mL/kg per mouse.

Example 3

(−) and (+) Enantiomers of O-Desmethyl Tramadol: Their Syntheses and the Preparation of Doses of O-Desmethyl Tramadol-with APAP First, O-desmethyl tramadol was prepared as set forth hereinafter. Diethylene glycol (125 mL) was added with cooling to potassium hydride (9.5 g) with the temperature being maintained at <50° C. To the solution was added thiophenol (10 mL) dissolved in diethylene glycol (25 mL), and then (−)-tramadol as the free base (9.3 g) in diethylene glycol (50 mL) was added. The final reaction mixture was heated slowly to reflux for 45 minutes. The mixture was cooled and then quenched into water. The pH was adjusted to about 3, and the mixture was extracted with ethyl ether. The pH was readjusted to about 8 and the resulting mixture was extracted 5 more times with methylene chloride. The extract was dried and the methylene chloride was evaporated to yield 4.6 g of the title compound as an oil. The oil was distilled (Kugelrohr), dissolved in tetrahydrofuran, treated with an ethanol/HCl solution to give 2.3 g of the salt. The salt was recrystallized from ethanol/ethyl ether and dried to yield 1.80 g of the salt of the (−) enantiomer of O-desmethyl tramadol (mp. 242°–3° C.), $[\alpha]_D^{25}$=−32.9 (C=1, EtOH).

C15H23NO2.HCl Theor.: C, 63.04; H, 8.46; N, 4.90 Found: C, 63.00; H, 8.51; N, 4.94

To prepare the (+) enantiomer of the title compound, the reaction was run under the same conditions except that (+)-tramadol as the free base was used instead of the (−)-tramadol to yield 2.8 g of the (+) enantiomer of O-desmethyl tramadol (mp. 242°–3° C.) $[\alpha]_D^{25}$=+32.2 (C=1, EtOH).

C15H23NO2.HCl Theor.: C, 63.04; H, 8.46; N, 4.90 Found: C, 63.14; H, 8.49; N, 4.86

The preparation of different ratios of a O-desmethyl/APAP combination is effected by first preparing a stock solution of O-desmethyl tramadol having a concentration expressed in $mg_{drugs}$ per 10 mL of distilled water. For example, 8 mg of O-desmethyl tramadol as the free base is dissolved per 10 mL of water to yield the highest dose of O-desmethyl tramadol stock solution. The stock solution of the O-desmethyl tramadol is then diluted with a sufficient amount of distilled water to prepare the lower doses of the O-desmethyl tramadol per 10 mL of distilled water. The combinations are then made by adding 10 mL of each dilution to the appropriate mg of APAP to achieve the desired ratio of O-desmethyl tramadol to APAP. For the 1:50 example: 400 mg of APAP as the free base is suspended with 10 mL of the 8 mg O-desmethyl tramadol solution and 2 drops of TWEEN 80, a pharmacological dispersant, manufactured by Fisher Scientific Company, to yield the 1:50 ratio, i.e., (8 mg: 400 mg) combination per 10 mL of water. Each ratio was prepared separately in a similar manner and injected in a volume of 10 ml/kg per mouse.

EXAMPLE 4

Analgesic Activity

Male CD1 mice (weighing from 18–24 g) were utilized in determining the analgesic effects associated with the compositions of the invention. The mice were all dosed orally with tramadol hydrochloride (calculated as the base), which was completely dissolved in distilled water, and acetaminophen (calculated as the base), which was completely dissolved in distilled water or in distilled water containing 2% by volume of Tween 80 containing 100% polysorbate 80. The dosing volume was 10 mL/kg.

The procedure used in detecting and comparing the analgesic activity of different classes of analgesia drugs for which there is a good correlation with human efficacy is the prevention of acetylcholine-induced abdominal constriction in mice (H. Collier et al., Br. J. Pharmacol., 32, 295 (1968)).

Mice, intubated with various doses of tramadol hydrochloride alone, acetaminophen alone, combined doses of tramadol hydrochloride and acetaminophen, or vehicle such as distilled water, or distilled water containing 2% by volume of Tween 80, were injected intraperitoneally with a challenge dose of acetylcholine bromide. The acetylcholine was completely dissolved in distilled water at a concentration of 5.5 mg/kg and injected at the rate of 0.20 mL/20 g. For scoring purposes an "abdominal constriction" was defined as a contraction of the abdominal musculature accompanied by arching of the back and extension of the limbs. The mice were observed 10 minutes for the presence or absence of the abdominal constriction response beginning immediately after receiving the acetylcholine dose, which was 30 minutes after receiving the oral administration of tramadol hydrochloride, acetaminophen, combined doses of tramadol hydrochloride and acetaminophen, or vehicle. Each mouse was used only once.

The analysis of possible superadditivity for the compositions at each fixed ratio was determined as disclosed by R. J. Tallarida et al., Life Sci., 45, 947 (1989). This procedure involved the determination of the total amount in the mixture that is required to produce a specified level of effect, such as 50% ($ED50_{mix}$), and the corresponding total amount that would be expected under simple additivity ($ED50_{add}$). Where it was established that $ED50_{mix}<ED50_{add}$ for a specific fixed-ratio, then that composition ratio was superadditive. Both the quantities $ED50_{mix}$ and $ED50_{add}$ were random variables; $ED50_{mix}$ was estimated from the dose-response curve for a specific fixed-ratio; $ED50_{add}$ was obtained by combining the ED50 estimates for the two drugs under additivity. $ED50_{mix}$ was then compared to $ED50_{add}$ via a Student's t-test. The ED50 value for tramadol hydrochloride alone was 5.5(4.8–6.4) mg/kg. The ED50 value for acetaminophen alone was 164.3 (122.7–219.9) mg/kg.

The interaction between tramadol and acetaminophen was determined at precise dosage ratios of tramadol hydrochloride and acetaminophen. Multiple (typically 4–6) coded doses of each selected combination were studied for analgesic effectiveness after 30 minutes using an experimental design which permitted the complete randomization of the separate dosage forms tested.

The interaction of tramadol hydrochloride and acetaminophen on the acetylcholine-induced abdominal constriction in mice was demonstrated by the data in Table I and is shown in the Loewe isobologram, FIG. I, (see, S. Loewe, Pharm. Rev., 9; 237 (1957) regarding the preparation and basis of an isobologram). In FIG. 1, the diagonal line joining the ED50 values of the two drugs given separately represents the simple additivity of effects at different component ratios. The dotted lines adjacent to the diagonal line define the 95% confidence interval. ED50 values falling under the curve (between the line and the origin) indicate superadditivity, i.e., unexpected enhancement of effects. The diagonal dashed lines radiating from the origin represent the dose ratios of APAP to tramadol hydrochloride used in mice receiving the combined drug dosages. The bars through the ED50 points for the tramadol and APAP composition represent the 95% confidence intervals of the ED50 value. The experimental data as represented in FIG. I establishes that composition having a ratio of tramadol to APAP from 1:1 to 1:1600 (represented by the curved line) give unexpectedly enhanced activity since $ED50_{mix}$ is less than $ED50_{add}$.

TABLE 1

| DRUG COMBINATIONS | DOSE (mg/kg, p.o.) | | | $ED_{50}$ 30 min (95% CI's) | |
|---|---|---|---|---|---|
| (Tramadol:APAP) | Tramadol | APAP | analgesia | Tramadol | APAP |
| tramadol only | 2 | 0 | 3/15 | | |
| | 3 | 0 | 4/15 | | |
| | 4 | 0 | 14/45 | | |
| | 6 | 0 | 20/45 | 5.5 | |
| | 8 | 0 | 40/60 | (4.8–6.4) | |
| | 10 | 0 | 15/15 | | |
| | 16 | 0 | 14/15 | | |

TABLE 1-continued

| DRUG COMBINATIONS | DOSE (mg/kg, p.o.) | | | $ED_{50}$ 30 min (95% CI's) | |
|---|---|---|---|---|---|
| (Tramadol:APAP) | Tramadol | APAP | analgesia | Tramadol | APAP |
| 1000:1 | 3.75 | 0.00375 | 1/13 | | |
| | 7.5 | 0.0075 | 8/15 | 7.0 | 0.01 |
| | 15 | 0.015 | 15/15 | (5.7–8.4) | (0.1–0.1) |
| 100:1 | 1.875 | 0.01875 | 0/15 | | |
| | 3.75 | 0.0375 | 4/15 | 6.9 | 0.1 |
| | 7.5 | 0.075 | 5/15 | (5.2–9.0) | (0.1–0.1) |
| | 15 | 0/15 | 15/15 | | |
| 20:1 | 1.875 | 0.09375 | 0.15 | | |
| | 3.75 | 0.1875 | 4/15 | 6.5 | 0.3 |
| | 7.5 | 0.375 | 7/15 | (5.1–8.3) | (0.3–0.4) |
| | 15 | 0.75 | 15/15 | | |
| 3:1 | 3.75 | 1.25 | 3/30 | | |
| | 7.5 | 2.5 | 12/30 | 7.8 | 2.6 |
| | 15 | 5 | 28/30 | (6.6–9.1) | (2.2–3.0) |
| 1:1 | 0.94 | 0.94 | 3/15 | | |
| | 1.875 | 1.875 | 8/30 | | |
| | 3.75 | 3.75 | 14/30 | 3.8 | 3.8 |
| | 5 | 5 | 12/28 | (3.0–4.8) | (3.0–4.8) |
| | 7.5 | 7.5 | 24/30 | | |
| | 15 | 15 | 15/15 | | |
| 1:3 | 3.75 | 11.25 | 7/30 | | |
| | 5 | 15 | 7/15 | 4.7 | 14.2 |
| | 7.5 | 22.5 | 29/30 | (4.3–5.2) | (12.8–15.7) |
| 1:5 | 2.5 | 12.5 | 7/30 | | |
| | 5 | 25 | 8/30 | 4.0 | 19.8 |
| | 10 | 50 | 30/30 | (3.3–4.7) | (16.7–23.4) |
| 1:5.7 | 0.47 | 2.66 | 0/15 | | |
| | 0.94 | 5.313 | 4/15 | | |
| | 1.88 | 10.625 | 1/15 | 4.1 | 23.3 |
| | 3.75 | 21.25 | 5/15 | (3.0–5.7) | (16.8–32.3) |
| | 7.5 | 42.5 | 11/15 | | |
| | 15 | 85 | 15/15 | | |
| 1:19 | 0.94 | 17.813 | 4/30 | | |
| | 1.88 | 36.625 | 10/28 | | |
| | 3.75 | 71.25 | 21/30 | 2.5 | 47.3 |
| | 5 | 95 | 22/30 | (2.0–3.0) | (38.9–57.5) |
| | 7.5 | 142.5 | 29/30 | | |
| | 15 | 285 | 15/15 | | |
| 1:50 | 0.25 | 12.5 | 3/30 | | |
| | 0.5 | 25 | 7/30 | | |
| | 1 | 50 | 9/30 | 1.2 | 61.4 |
| | 2 | 100 | 19/30 | (1.0–1.5) | (49.0–77.1) |
| | 4 | 200 | 27/30 | | |
| | 8 | 400 | 30/30 | | |
| 1:100 | 0.25 | 25 | 3/60 | | |
| | 0.5 | 50 | 12/60 | | |
| | 1 | 100 | 19/60 | 1.1 | 111.3 |
| | 2 | 200 | 51/60 | (1.0–1.3) | (96.4–128.6) |
| | 4 | 400 | 55/60 | | |
| | 8 | 800 | 30/30 | | |
| 1:200 | 0.125 | 25 | 1/60 | | |
| | 0.25 | 50 | 9/60 | | |
| | 0.5 | 100 | 27/60 | 0.6 | 129.7 |
| | 1 | 200 | 44/60 | (0.6–0.8) | (110.4–152.4) |
| | 2 | 400 | 48/60 | | |
| | 4 | 800 | 30/30 | | |
| 1:400 | 0.0625 | 25 | 2/15 | | |
| | 0.125 | 50 | 4/30 | | |
| | 0.25 | 100 | 18/30 | 0.2 | 95.1 |
| | 0.5 | 200 | 12/15 | (0.2–0.3) | (75.4–119.8) |
| | 1 | 400 | 28/30 | | |
| | 2 | 800 | 15/15 | | |
| 1:800 | 0.03125 | 25 | 4/30 | | |
| | 0.0625 | 50 | 9/30 | | |
| | 0.125 | 100 | 15/30 | 0.1 | 77.4 |
| | 0.25 | 200 | 27/30 | (0.1–0.1) | (62.9–95.2) |
| | 0.5 | 400 | 30/30 | | |
| 1:1600 | 0.03125 | 50 | 2/30 | | |
| | 0.0625 | 100 | 14/30 | | |
| | 0.125 | 200 | 22/30 | 0.1 | 125.7 |
| | 0.25 | 400 | 27/30 | (0.1–0.1) | (102.7–153.8) |
| | 0.5 | 800 | 30/30 | | |
| APAP only | 0 | 30 | 2/15 | | |
| | 0 | 40 | 12/43 | | |
| | 0 | 50 | 1/15 | | |

TABLE 1-continued

| DRUG COMBINATIONS | DOSE (mg/kg, p.o.) | | | $ED_{50}$ 30 min (95% CI's) | |
|---|---|---|---|---|---|
| (Tramadol:APAP) | Tramadol | APAP | analgesia | Tramadol | APAP |
| | 0 | 60 | 8/30 | | |
| | 0 | 80 | 23/60 | | |
| | 0 | 100 | 13/30 | — | 164.3 |
| | 0 | 120 | 13/30 | | (122.7–219.9) |
| | 0 | 160 | 10/30 | | |
| | 0 | 200 | 13/25 | | |
| | 0 | 240 | 14/25 | | |
| | 0 | 400 | 12/15 | | |
| | 0 | 800 | 13/15 | | |

We claim:

[1. A pharmaceutical composition comprising a tramadol material and acetaminophen, wherein the ratio of the tramadol material to acetaminophen is a weight ratio from about 1:1 to about 1:1600.]

[2. The pharmaceutical composition of claim 1 wherein the tramadol material is tramadol hydrochloride.]

[3. The pharmaceutical composition of claim 2 wherein the tramadol hydrochloride is racemic.]

[4. The pharmaceutical composition of claim 1 wherein the weight ratio is about 1:1.]

[5. The pharmaceutical composition of claim 1 wherein the weight ratio is from about 1:5 to about 1:1600.]

6. [The pharmaceutical composition of claim 5 wherein the] *A pharmaceutical composition comprising a tramadol material and acetaminophen, wherein the ratio of the tramadol material to acetaminophen is a* weight ratio [is] *of* about 1:5.

[7. The pharmaceutical composition of claim 5 wherein the weight ratio is from about 1:19 to about 1:800.]

[8. The pharmaceutical composition of claim 7 wherein the weight ratio is from about 1:19 to about 1:50.]

[9. The pharmaceutical composition of claim 1 further comprising a pharmaceutically acceptable carrier.]

[10. The pharmaceutical composition of claim 1 further comprising a decongestant or bronchodilator.]

[11. The pharmaceutical composition of claim 1 further comprising an antitussive.]

[12. The pharmaceutical composition of claim 1 further comprising an antihistamine or a non-sedating antihistamine.]

[13. The pharmaceutical composition of claim 1 further comprising a muscle relaxant.]

[14. The pharmaceutical composition of claim 1 further comprising a sleep aid.]

15. A method for treating [a] pain in a mammal comprising [an administration] *administering* to the mammal an effective amount of the pharmaceutical composition of [claim 1] *claim 6*.

*16. A pharmaceutical composition comprising an active ingredient that consists essentially of tramadol and acetaminophen, wherein the ratio of tramadol to acetaminophen is a weight ratio from about 1:1 to about 1:1600.*

*17. The pharmaceutical composition of claim 16 wherein the tramadol is racemic.*

*18. The pharmaceutical composition of claim 16 wherein the tramadol is present as its hydrochloride salt.*

*19. The pharmaceutical composition of claim 18 wherein the tramadol hydrochloride is racemic.*

*20. The pharmaceutical composition of claim 16 wherein said active ingredient consists essentially of an admixture of said tramadol and said acetaminophen.*

*21. The pharmaceutical composition of claim 16 wherein the weight ratio is about 1:1.*

*22. The pharmaceutical composition of claim 16 wherein the weight ratio is from about 1:5 to about 1:1600.*

*23. The pharmaceutical composition of claim 16 wherein the weight ratio is about 1:5.*

*24. The pharmaceutical composition of claim 16 comprising a pharmaceutically acceptable carrier.*

*25. The pharmaceutical composition of claim 16 that is in the form of a powder.*

*26. The pharmaceutical composition of claim 16 that is in the form of a capsule.*

*27. The pharmaceutical composition of claim 16 that is in the form of a tablet.*

*28. The pharmaceutical composition of claim 16 that is in the form of a suspension.*

*29. The pharmaceutical composition of claim 16 that is in the form of a solution.*

*30. A method for treating pain in a mammal comprising administering to the mammal an effective amount of the pharmaceutical composition of claim 16.*

*31. A pharmaceutical composition comprising an active ingredient that consists essentially of tramadol and acetaminophen, wherein the ratio of tramadol to acetaminophen is a weight ratio from about 1:5 to about 1:50.*

*32. The pharmaceutical composition of claim 31 wherein the tramadol is racemic.*

*33. The pharmaceutical composition of claim 31 wherein the tramadol is present as its hydrochloride salt.*

*34. The pharmaceutical composition of claim 33 wherein the tramadol hydrochloride is racemic.*

*35. The pharmaceutical composition of claim 31 wherein said active ingredient consists essentially of an admixture of said tramadol and said acetaminophen.*

*36. The pharmaceutical composition of claim 31 comprising a pharmaceutically acceptable carrier.*

*37. The pharmaceutical composition of claim 31 that is in the form of a powder.*

*38. The pharmaceutical composition of claim 31 that is in the form of a capsule.*

*39. The pharmaceutical composition of claim 31 that is in the form of a tablet.*

*40. The pharmaceutical composition of claim 31 that is in the form of a suspension.*

*41. The pharmaceutical composition of claim 31 that is in the form of a solution.*

*42. A method for treating pain in a mammal comprising administering to the mammal an effective amount of the pharmaceutical composition of claim 31.*

*43. A pharmaceutical composition comprising an active ingredient that consists essentially of tramadol and acetaminophen, wherein the ratio of tramadol to acetaminophen is a weight ratio from about 1:5 to about 1:19.*

*44. The pharmaceutical composition of claim 43 wherein the tramadol is racemic.*

*45. The pharmaceutical composition of claim 43 wherein the tramadol is present as its hydrochloride salt.*

*46. The pharmaceutical composition of claim 45 wherein the tramadol hydrochloride is racemic.*

*47. The pharmaceutical composition of claim 43 wherein said active ingredient consists essentially of an admixture of said tramadol and said acetaminophen.*

*48. The pharmaceutical composition of claim 43 comprising a pharmaceutically acceptable carrier.*

*49. The pharmaceutical composition of claim 43 that is in the form of a powder.*

*50. The pharmaceutical composition of claim 43 that is in the form of a capsule.*

*51. The pharmaceutical composition of claim 43 that is in the form of a tablet.*

*52. The pharmaceutical composition of claim 43 that is in the form of a suspension.*

*53. The pharmaceutical composition of claim 43 that is in the form of a solution.*

*54. A method for treating pain in a mammal comprising administering to the mammal an effective amount of the pharmaceutical composition of claim 43.*

*55. A pharmaceutical composition comprising an active ingredient that consists essentially of tramadol and acetaminophen, wherein the ratio of tramadol to acetaminophen is a weight ratio from about 1:19 to about 1:50.*

*56. The pharmaceutical composition of claim 55 wherein the tramadol is racemic.*

*57. The pharmaceutical composition of claim 55 wherein the tramadol is present as its hydrochloride salt.*

*58. The pharmaceutical composition of claim 57 wherein the tramadol hydrochloride is racemic.*

*59. The pharmaceutical composition of claim 55 wherein said active ingredient consists essentially of an admixture of said tramadol and said acetaminophen.*

*60. The pharmaceutical composition of claim 55 comprising a pharmaceutically acceptable carrier.*

*61. The pharmaceutical composition of claim 55 that is in the form of a powder.*

*62. The pharmaceutical composition of claim 55 that is in the form of a capsule.*

*63. The pharmaceutical composition of claim 55 that is in the form of a tablet.*

*64. The pharmaceutical composition of claim 55 that is in the form of a suspension.*

*65. The pharmaceutical composition of claim 55 that is in the form of a solution.*

*66. A method for treating pain in a mammal comprising administering to the mammal an effective amount of the pharmaceutical composition of claim 55.*

*67. A pharmaceutical composition consisting essentially of:*

*an active ingredient that consists of racemic tramadol hydrochloride and acetaminophen, wherein the ratio of racemic tramadol hydrochloride to acetaminophen is from about 1:5 to about 1:19; and*

*a pharmaceutically acceptable carrier.*

*68. The pharmaceutical composition of claim 67 that is in the form of a capsule.*

*69. The pharmaceutical composition of claim 67 that is in the form of a tablet.*

*70. The pharmaceutical composition of claim 67 that is in the form of a suspension.*

*71. The pharmaceutical composition of claim 67 that is in the form of a solution.*

*72. A method for treating pain in a mammal comprising orally administering to the mammal an effective amount of the pharmaceutical composition of claim 67.*

*73. A method for treating pain in a mammal comprising orally administering to the mammal an effective amount of the pharmaceutical composition of claim 68.*

*74. A method for treating pain in a mammal comprising orally administering to the mammal an effective amount of the pharmaceutical composition of claim 69.*

*75. A method for treating pain in a mammal comprising orally administering to the mammal an effective amount of the pharmaceutical composition of claim 70.*

*76. A method for treating pain in a mammal comprising orally administering to the mammal an effective amount of the pharmaceutical composition of claim 71.*

* * * * *

UNITED STATES PATENT AND TRADEMARK OFFICE

CERTIFICATE OF CORRECTION

PATENT NO. : RE 39,221 E
APPLICATION NO. : 10/761096
DATED : August 1, 2006
INVENTOR(S) : Robert B. Raffa et al.

It is certified that error appears in the above-identified patent and that said Letters Patent is hereby corrected as shown below:

Title Page,
Item (56), References Cited,

OTHER PUBLICATIONS:
"In the United States District Court for the District of New Jersey, Civil Action No. 04-886 (HAA)" reference, delete "Demand for Jury Trail (Mar. 19, 2004)" and insert -- Demand for Jury Trial (Mar. 19, 2004) --.
"Merck Index," reference, delete "(No. 49)" and insert-- (No. 40) --.
"Senn, H.J.," reference, delete "in de Onkologie" and insert -- in der Onkologie --.
"Staritz M., et al.," reference, delete "Gut, 190, 31, 222-225" and insert -- Gut, 1990, 31, 222-225 --.
"Wörz R.," reference (second occurrence), delete "Medikamentoöse" and insert -- Medikamentöse --.

Signed and Sealed this

Tenth Day of April, 2007

JON W. DUDAS
*Director of the United States Patent and Trademark Office*